(12) United States Patent
Singh et al.

(10) Patent No.: US 9,056,069 B2
(45) Date of Patent: *Jun. 16, 2015

(54) CANCER THERAPY BASED ON TUMOR ASSOCIATED ANTIGENS DERIVED FROM CYCLIN D1

(75) Inventors: Harpreet Singh, Tuebingen (DE); Toni Weinschenk, Aichwald (DE); Steffen Walter, Reutlingen (DE)

(73) Assignee: IMMATICS BIOTECHNOLOGIES GMBH, Tuebingen (DE)

( * ) Notice: Subject to any disclaimer, the term of this patent is extended or adjusted under 35 U.S.C. 154(b) by 256 days.

This patent is subject to a terminal disclaimer.

(21) Appl. No.: 13/150,785

(22) Filed: Jun. 1, 2011

(65) Prior Publication Data

US 2012/0027684 A1 Feb. 2, 2012

Related U.S. Application Data

(60) Provisional application No. 61/350,731, filed on Jun. 2, 2010.

(30) Foreign Application Priority Data

Jun. 2, 2010 (GB) .................................. 1009222.9

(51) Int. Cl.
| | |
|---|---|
| A61K 39/00 | (2006.01) |
| A61K 38/20 | (2006.01) |
| A61K 38/21 | (2006.01) |
| A61K 45/06 | (2006.01) |
| C07K 14/47 | (2006.01) |
| A61K 31/404 | (2006.01) |
| A61K 31/44 | (2006.01) |
| A61K 31/675 | (2006.01) |
| A61K 39/39 | (2006.01) |
| C12N 5/0783 | (2010.01) |
| A61K 38/17 | (2006.01) |
| A61K 38/19 | (2006.01) |

(52) U.S. Cl.
CPC ......... *A61K 39/0011* (2013.01); *A61K 38/2013* (2013.01); *A61K 38/2026* (2013.01); *A61K 38/21* (2013.01); *A61K 45/06* (2013.01); *C07K 14/4738* (2013.01); *G01N 2800/24* (2013.01); *G01N 2800/7028* (2013.01); *A61K 31/404* (2013.01); *A61K 31/44* (2013.01); *A61K 31/675* (2013.01); *A61K 38/20* (2013.01); *A61K 39/39* (2013.01); *C12N 5/0638* (2013.01); *A61K 38/1709* (2013.01); *A61K 38/193* (2013.01)

(58) Field of Classification Search
None
See application file for complete search history.

(56) References Cited

U.S. PATENT DOCUMENTS

| 7,833,970 | B2 | 11/2010 | Dengjel | |
|---|---|---|---|---|
| 7,994,276 | B2 | 8/2011 | Singh et al. | |
| 8,067,529 | B2 | 11/2011 | Rammensee et al. | |
| 2005/0222390 | A1* | 10/2005 | Weinschenk et al. | ......... 530/350 |
| 2009/0004213 | A1 | 1/2009 | Singh et al. | |
| 2009/0274714 | A1 | 11/2009 | Singh et al. | |
| 2013/0177525 | A1* | 7/2013 | Singh et al. | .................. 424/85.2 |

FOREIGN PATENT DOCUMENTS

| EP | 1 642 905 | | 4/2006 | | |
|---|---|---|---|---|---|
| EP | 1 760 088 | | 3/2007 | | |
| EP | 1 760 089 | | 3/2007 | | |
| WO | 95/18145 | | 7/1995 | | |
| WO | 2005/035714 | | 4/2005 | | |
| WO | WO 2007/028573 | * | 3/2007 | ............. | C07K 14/47 |
| WO | 2009/015841 A1 | | 2/2009 | | |
| WO | WO 2009/059011 | * | 5/2009 | ............ | C07K 14/435 |
| WO | WO 2010/104749 A2 | * | 9/2010 | ............. | C12N 15/62 |

OTHER PUBLICATIONS

Celis (J. of Clinical Investigation, 2002, 110:1765-1768).*
Marincola et al. (Trends in Immunology, Jun. 2003, 334-341).*
Kirkin et al. (1998, APMIS, 106: 665-679).*
Sherman et al. (Critical Reviews in Immunol. 1998, 18:47-54).*
Smith (Clin. Immunol, 1994, 41(4): 841-849).*
Harlin et al. (Caner Immunol. Immunotherap. 2006, 55:1185-1197).*
Gura (Science, 1997, 278:1041-1042).*
Kaiser (Science, 2006, 313: 1370).*
Taber's Cyclopedic Medical Dictionary (1985, F.A. Davis Company, Philadelphia, p. 274).*
Krontiris and Capizzi (Internal Medicine, 4th Edition, Editor-in-chief Jay Stein, Elsevier Science, 1994 Chapters 71-72, pp. 699-729).*
Liu et al. (Cancer Immunol. Immunother. 2007 56:1597-1604).*
MacLean et al. (J. Immunother Emphasis Tumor Immunol. Jul. 1996, 19(4): 309-16).*
International Preliminary Report on Patentability and Written Opinion Based on Application No. PCT/EP2011/059121 Mailed Dec. 4, 2012.
Cheever et al.; "T-Cell Immunity to Oncogenic Proteins Includng Mutated RAS and Chimeric BCR-Ablalpha"; Ann NY Acad Sci; Aug. 12, 1993; vol. 690; pp. 101-112; Blackwell Publishing.
Zeh III et al.; "High Avidity CTLS for Two Self-Antigens Demonstrate Superior in Vitro and in Vivo Antitumor Efficacy"; The Journal of Immunology; 1999; vol. 162; pp. 989-994.
Schubert et al.; Rapid Degradation of a Large Fraction of Newly Synthesized Proteins by Proteasomes; Nature; 2000; vol. 404; No. 6779; pp. 770-774, MacMillan Magazines Ltd.

(Continued)

Primary Examiner — Peter J Reddig
(74) Attorney, Agent, or Firm — Miles & Stockbridge PC

(57) ABSTRACT

The present invention relates to cyclin D1-derived peptides for use in the improved treatment of cancer in a patient, particularly in the form of a combination therapy using a vaccine. Other aspects relate to the use of the peptides or a combination thereof as a diagnostic tool.

15 Claims, 8 Drawing Sheets

(56) References Cited

OTHER PUBLICATIONS

Cresswell; "Assembly, Transport, and Function of MHC Class II Molecules"; Annu. Rev. Immunol.; 1994; vol. 12; pp. 259-293; Annual Reviews Inc.

Kobayashi et al.; "Identification of an Antigenic Epitope for Helper T Lymphocytes From Carcinoembryonic Antigen1"; Clinical Cancer Research; vol. 8; Oct. 2002; pp. 3219-3225; American Association for Cancer Research.

Gnjatic et al.; "Survey of Naturally Occurring CD4+ T Cell Responses Against NY-ESO-1 in Cancer Patients: Correlation With Antibody Responses"; PNAS; Jul. 22, 2003; vol. 100; No. 15; pp. 8862-8867.

Qin et al.; "A Critical Requirement of Interferon Gamma-Mediated Angiostasis for Tumor Rejection by CD8+ T Cells"; Cancer Research; vol. 63; Jul. 15, 2003; pp. 4095-4100.

Dengjel et al.; "Unexpected Abundance of HLA Class II Presented Peptides in Primary Renal Cell Carcinomas"; Clin Cancer Res.; 2006; vol. 12; No. 14; pp. 4163-4170; American Association for Cancer Research.

Mach et al.; "Regulation of MHC Class II Genes: Lessons From a Disease"; Annu. Rev. Immunol.; 1996; vol. 14; pp. 301-331; Annual Reviews Inc.

Vigneron et al.; "An Antigenic Peptide Produced by Peptide Splicing in the Proteasome"; Science; vol. 304; Apr. 23, 2004; pp. 587-590.

Lemmel et al.; "Differential Quantitative Analysis of MHC Ligands by Mass Spectrometry Using Stable Isotope Labeling"; Nature Biotechnology; Apr. 2004; vol. 22; No. 4; p. 450-454.

Weinschenk et al.; "Integrated Functional Genomics Approach for the Design of Patient-Individual Antitumor Vaccines1"; Cancer Research; vol. 62; Oct. 15, 2002; pp. 5818-5827; American Association for Cancer Research.

Lew et al.; "Isolation of Three Novel Human Cyclins by Rescue of G1 Cyclin (CLN) Function in Yeast"; Cell; vol. 66; September 20, 1991; pp. 1197-1206; Cell Press.

Xiong et al.; "Human D-Type Cyclin"; Cell; vol. 65; May 17, 1991; pp. 691-699; Cell Press.

Deshpande et al.; "Cyclins and CDKS in Development and Cancer: A Perspective"; Oncogene; 2005; vol. 24; pp. 2909-2915; Nature Publishing Group.

Bates et al.; "CDK6 (PLSTIRE) and CDK4 {PSK-J3) are a Distinct Subset of the Cyclin-Dependent Kinases that Associate with Cyclin D1"; Oncogene; 1994; vol. 9; pp. 71-79; MacMillan Press Ltd.

Hedberg et al.; "Cyclin-D1 Expression in Human Renal-Cell Carcinoma"; Int. J. Cancer (Pred. Oncol.); vol. 84; 1999; pp. 268-272; Wiley-Liss, Inc.

Vasef et al.; "Expression of Cyclin D1 in Parathyroid Carcinomas, Adenomas, and Hyperplasias: A Paraffin Immunohistochemical Study"; Mod Pathol; 1999; vol. 12; No. 4; pp. 412-416; The United States and Canadian Academy of Pathology, Inc.

Troussard et al.; "Cyclin D1 Expression in Patients With Multiple Myeloma"; The Hematology Journal; 2000; vol. 1; pp. 181-185; The European Hematology Association.

Wang et al.; "Cyclin D1 As a Universally Expressed Mantle Cell Lymphoma-Associated Tumor Antigen for Immunotherapy"; Leukemia; 2009; vol. 23; pp. 1320-1328; MacMillan Publishers Limited.

Kondo et al.; "Cyclin D1—Specific Cytotoxic T Lymphocytes are Present in the Repertoire of Cancer Patients: Implications for Cancer Immunotherapy"; Clin Cancer Res; Oct. 15, 2008; vol. 14; No. 20; pp. 6574-6579.

Fu et al.; "Minireview: Cyclin D1: Normal and Abnormal Functions"; Endocrinology; Dec. 2004; Vol. 145; No. 12; pp. 5439-5547; The Endocrine Society.

Yu et al.; "Association of the Cyclin D1 Gene G870 Polymorphism With Susceptability to Sporadic Renal Cell Carcinoma"; The Journal of Urology; vol. 172; Dec. 2004; pp. 2410-2413.

Maeda et al. "Cyclin D1 Overexpression and Prognosis in Colorectal Adenocarcinoma"; Oncology; 1998; vol. 55; pp. 145-151; S. Karger AG.

McKay et al.; "Cyclin D1 Protein Expression and Gene Polymorphism in Colorectal Cancer"; Int. J. Cancer; vol. 88; 2000; pp. 77-81; Wiley-Liss, Inc.

Bahnassy et al.; "Cyclin A and Cyclin D1 As Significant Prognostic Markers in Colorectal Cancer Patients"; BMC Gastroenterology; 2004; vol. 4; No. 22; pp. 1-12.

Balcerczak et al.; "Cyclin D1 Protein and CCND1 Gene Expression in Colorectal Cancer"; EJSO; 2005; vol. 31; pp. 721-726; Elsevier Ltd.

Shtutman et al.; The Cyclin D1 Gene is a Target of the Beta-Catenin/LEF-1 Pathway; Proc. Natl. Acad. Sci.; USA; vol. 96; May 1999; pp. 5522-5527; Cell Biology.

Tetsu et al.; "Beta-Catenin Regulates Expression of Cyclin D1 in Colon Carcinoma Cells"; Nature; vol. 398; Apr. 1, 1999; pp. 422-426; MacMillan Magazines Ltd.

Sadovnikova et al.; "Generation of Human Tumor-Reactive Cytotoxic T Cells Against Peptides Presented by Non-Self HLA Class I Molecules"; Eur. J. Immunol.; 1998; vol. 28; pp. 193-200; Wiley-VCH.

Kondo et al.; "CD40-Activated B Cells Can Be Generated in High Number and Purity in Cancer Patients: Analysis of Immunogenicity and Homing Potential"; Clinical and Experimental Immunology; 2008; vol. 155; pp. 249-256; British Socirty for Immunology.

Kondo et al.; "Using CD40-Activated B Cells to Efficiently Identify Epitopes of Tumor Antigens"; J Immunother; vol. 32; No. 2; Feb.-Mar. 2009; pp. 157-160; Lippincott Williams & Wilkins.

Buchner et al.; "Phase 1 Trial of Allogeneic Gene-Modified Tumor Cell Vaccine RCC-26/CD80/IL-2 in Patients with Metastatic Renal Cell Carcinoma"; Human Gene Therapy; vol. 21; Mar. 2010; pp. 258-287; Mary Ann Liebert, Inc.

Strubin et al.; The Complete Sequence of the MRNA for the HLA-DR-Associated Invariant Chain Reveals a Polypeptide With an Unusual Transmembrane Polarity; EMBO J.; 1984; vol. 3; No. 4; pp. 869-872; IRL Press Limited.

Rammensee et al.; "SYFPEITHI: Database for MHC Ligands and Peptide Motifs"; Immunogenetics; 1999; vol. 50; pp. 213-219; Springer-Verlag.

"Prediction Algorithm for Proteasomal Cleavages"; Last Updated Apr. 22, 2005; http://Paproc.de/.

Institute for Cel Biology Department of Immunology; BMI Heidelberg; A Database of MHC Ligands and Peptide Motifs (Ver. 1.0); Last Updated Aug. 2, 2009; http/www.syfpeithi.de.

Meziere, et al.; "In Vivo T Helper Cell Response to Retro-Inverso Peptidomimetics1"; J. Immunol.; 1997; vol. 159; pp. 3230-3237; The American Association of Immunologists.

Longenecker, et al.; "Immune Responses of Mice and Human Breast Cancer Patients Following Immunization with Synthetic Sialyl-TN Conjugated to KLH Plus Detox Adjuvant"; Ann. NY Acad. Sci.; 1993; vol. 690; pp. 276-291.

Brinkman et al.; "Peptide-Based Vaccines for Cancer Immunotherapy"; Peptides, Proteins & Antisense; Expert Opin. Biol. Ther. 2004; vol. 4; No. 2; pp. 181-198; Ashley Publications Ltd.

Zhou et al.; "A Distinct Pattern of Cytokine Gene Expression by Human CD83+ Blood Dendritic Cells"; Blood; vol. 86; No. 9; Nov. 1, 1995; pp. 3295-3301; The American Society of Hematology.

Roth et al.; "Activation of Cloned Human CD4+ TH1 and TH2 Cells by Blood Dendritic Cells"; Scand. J. Immunol; 43; 1996; pp. 646-651; Blackwell Science Ltd.

Lu, et al.; "Improved Synthesis of 4-Alkoxybenzyl Alcohol Resin"; J. Org. Chem.; 1981; vol. 46: pp. 3433-3436; American Chemical Society.

Bruckdorfer et al.; "From Production of Peptides in Milligram Amounts for Research to Multi-Tons Quantities for Drugs of the Future"; Current Pharmaceutical Biotechnology; 2004; vol. 5; pp. 29-43; Bentham Science Publishers Ltd.

Weinschenk et al,; "Integrated Functional Genomics Approach for the Design of Patient-Individual Antitumor Vaccines1"; Cancer Research; vol. 62; Oct. 15, 2002; pp. 5818-5827; American Association for Cancer Research.

Rammensee et al.; "MHC Ligands and Peptide Motifs"; 1997; Springer-Verlag GmbH; Landes Bioscience; p. 1-462.

Heimburg-Molinaro et al., Cancer Vaccines and Carbohydrate Epitopes, Vaccine, vol. 29, issue 48, 8802-8826, PMC Author manuscript pp. 1-57 (Nov. 8, 2012).

Palucka et al., Dendritic Cells: a critical player in cancer therapy?, J. Immunotherapy vol. 31, issue 9, pp. 793-805, Author's Manuscript at pp. 1-23 (Nov. 1, 2009).

* cited by examiner

```
  1 MEHQLLCCEV ETIRRAYPDA NLLNDRVLRA MLKAEETCAP SVSYFKCVQK EVLPSMRKIV
                             CCN-E                              CCN-I

61 ATWMLEVCEE QKCEEEVFPL AMNYLDRFLS LEPVKKSRLQ LLGATCMFVA SKMKETIPLT
      CCN-A      CCN-004 AND F1 TO F3            CCN-001      CCN-006

121 AEKLCIYTDN SIRPEELLQM ELLLVNKLKW NLAAMTPHDF IEHFLSKMPE AEENKQIIRK
                             CCN-H                           CCN-J

181 HAQTFVALCA TDVKFISNPP SMVAAGSVVA AVQGLNLRSP NNFLSYYRLT RFLSRVIKCD
                CCN-003   CCN-B TO D AND G                   CCN-002

241 PDCLRACQEQ IEALLESSLR QAQQNMDPKA AEEEEEEEEE VDLACTPTDV RDVDI
       CCN-007
```

FIG. 1

SEQUENCE LISTING

```
<160> NUMBER OF SEQ ID NOS: 27

<210> SEQ ID NO 1
<211> LENGTH: 9
<212> TYPE: PRT
<213> ORGANISM: Homo sapiens

<400> SEQUENCE: 1

Leu Leu Gly Ala Thr Cys Met Phe Val
1               5

<210> SEQ ID NO 2
<211> LENGTH: 9
<212> TYPE: PRT
<213> ORGANISM: Homo sapiens

<400> SEQUENCE: 2

Arg Leu Thr Arg Phe Leu Ser Arg Val
1               5

<210> SEQ ID NO 3
<211> LENGTH: 15
<212> TYPE: PRT
<213> ORGANISM: Homo sapiens

<400> SEQUENCE: 3

Asn Pro Pro Ser Met Val Ala Ala Gly Ser Val Val Ala Ala Val
1               5                   10                  15
```

```
<210> SEQ ID NO 4
<211> LENGTH: 9
<212> TYPE: PRT
<213> ORGANISM: Homo sapiens

<400> SEQUENCE: 4

Glu Val Phe Pro Leu Ala Met Asn Tyr
1               5

<210> SEQ ID NO 5
<211> LENGTH: 10
<212> TYPE: PRT
<213> ORGANISM: Homo sapiens

<400> SEQUENCE: 5

Glu Thr Ile Pro Leu Thr Ala Glu Lys Leu
1               5                   10

<210> SEQ ID NO 6
<211> LENGTH: 10
<212> TYPE: PRT
<213> ORGANISM: Homo sapiens

<400> SEQUENCE: 6

Ala Leu Leu Glu Ser Ser Leu Arg Gln Ala
1               5                   10

<210> SEQ ID NO 7
<211> LENGTH: 9
<212> TYPE: PRT
<213> ORGANISM: Homo sapiens

<400> SEQUENCE: 7

Ile Val Ala Thr Trp Met Leu Glu Val
1               5

<210> SEQ ID NO 8
<211> LENGTH: 9
<212> TYPE: PRT
<213> ORGANISM: Homo sapiens

<400> SEQUENCE: 8

Ser Val Val Ala Ala Val Gln Gly Leu
1               5

<210> SEQ ID NO 9
<211> LENGTH: 11
<212> TYPE: PRT
<213> ORGANISM: Homo sapiens

<400> SEQUENCE: 9

Ser Val Val Ala Ala Val Gln Gly Leu Asn Leu
1               5                   10

<210> SEQ ID NO 10
<211> LENGTH: 9
<212> TYPE: PRT
<213> ORGANISM: Homo sapiens

<400> SEQUENCE: 10

Asn Tyr Leu Asp Arg Phe Leu Ser Leu
1               5
```

```
<210> SEQ ID NO 11
<211> LENGTH: 8
<212> TYPE: PRT
<213> ORGANISM: Homo sapiens

<400> SEQUENCE: 11

Asp Arg Val Leu Arg Ala Met Leu
1               5

<210> SEQ ID NO 12
<211> LENGTH: 9
<212> TYPE: PRT
<213> ORGANISM: Homo sapiens

<400> SEQUENCE: 12

Glu Glu Glu Val Phe Pro Leu Ala Met
1               5

<210> SEQ ID NO 13
<211> LENGTH: 10
<212> TYPE: PRT
<213> ORGANISM: Homo sapiens

<400> SEQUENCE: 13

Glu Glu Val Phe Pro Leu Ala Met Asn Tyr
1               5                   10

<210> SEQ ID NO 14
<211> LENGTH: 10
<212> TYPE: PRT
<213> ORGANISM: Homo sapiens

<400> SEQUENCE: 14

Glu Val Phe Pro Leu Ala Met Asn Tyr Leu
1               5                   10

<210> SEQ ID NO 15
<211> LENGTH: 11
<212> TYPE: PRT
<213> ORGANISM: Homo sapiens

<400> SEQUENCE: 15

Asn Leu Arg Ser Pro Asn Asn Phe Leu Ser Tyr
1               5                   10

<210> SEQ ID NO 16
<211> LENGTH: 8
<212> TYPE: PRT
<213> ORGANISM: Homo sapiens

<400> SEQUENCE: 16

Val Asn Lys Leu Lys Trp Asn Leu
1               5

<210> SEQ ID NO 17
<211> LENGTH: 9
<212> TYPE: PRT
<213> ORGANISM: Homo sapiens

<400> SEQUENCE: 17

Val Gln Lys Glu Val Leu Pro Ser Met
1               5
```

```
<210> SEQ ID NO 18
<211> LENGTH: 11
<212> TYPE: PRT
<213> ORGANISM: Homo sapiens

<400> SEQUENCE: 18

Met Pro Glu Ala Glu Glu Asn Lys Gln Ile Ile
1               5                   10

<210> SEQ ID NO 19
<211> LENGTH: 9
<212> TYPE: PRT
<213> ORGANISM: Homo sapiens

<400> SEQUENCE: 19

Tyr Val Asp Pro Val Ile Thr Ser Ile
1               5

<210> SEQ ID NO 20
<211> LENGTH: 9
<212> TYPE: PRT
<213> ORGANISM: Homo sapiens

<400> SEQUENCE: 20

Ser Thr Ala Pro Pro Val His Asn Val
1               5

<210> SEQ ID NO 21
<211> LENGTH: 9
<212> TYPE: PRT
<213> ORGANISM: Homo sapiens

<400> SEQUENCE: 21

Leu Leu Leu Leu Thr Val Leu Thr Val
1               5

<210> SEQ ID NO 22
<211> LENGTH: 9
<212> TYPE: PRT
<213> ORGANISM: Homo sapiens

<400> SEQUENCE: 22

Tyr Leu Ser Gly Ala Asn Leu Asn Leu
1               5

<210> SEQ ID NO 23
<211> LENGTH: 9
<212> TYPE: PRT
<213> ORGANISM: Homo sapiens

<400> SEQUENCE: 23

Tyr Leu Ser Gly Ala Asp Leu Asn Leu
1               5

<210> SEQ ID NO 24
<211> LENGTH: 16
<212> TYPE: PRT
<213> ORGANISM: Homo sapiens

<400> SEQUENCE: 24

Ser Pro Gln Tyr Ser Trp Arg Ile Asn Gly Ile Pro Gln Gln His Thr
1               5                   10                  15
```

<210> SEQ ID NO 25
<211> LENGTH: 10
<212> TYPE: PRT
<213> ORGANISM: Homo sapiens

<400> SEQUENCE: 25

Ala Leu Phe Val Arg Leu Leu Ala Leu Ala
1               5                   10

<210> SEQ ID NO 26
<211> LENGTH: 15
<212> TYPE: PRT
<213> ORGANISM: Homo sapiens

<400> SEQUENCE: 26

Thr Leu Gly Glu Phe Leu Lys Leu Asp Arg Glu Arg Ala Lys Asn
1               5                   10                  15

<210> SEQ ID NO 27
<211> LENGTH: 295
<212> TYPE: PRT
<213> ORGANISM: Homo sapiens

<400> SEQUENCE: 27

Met Glu His Gln Leu Leu Cys Cys Glu Val Glu Thr Ile Arg Arg Ala
1               5                   10                  15

Tyr Pro Asp Ala Asn Leu Leu Asn Asp Arg Val Leu Arg Ala Met Leu
                20                  25                  30

Lys Ala Glu Glu Thr Cys Ala Pro Ser Val Ser Tyr Phe Lys Cys Val
            35                  40                  45

Gln Lys Glu Val Leu Pro Ser Met Arg Lys Ile Val Ala Thr Trp Met
        50                  55                  60

Leu Glu Val Cys Glu Glu Gln Lys Cys Glu Glu Val Phe Pro Leu
65                  70                  75                  80

Ala Met Asn Tyr Leu Asp Arg Phe Leu Ser Leu Glu Pro Val Lys Lys
                85                  90                  95

Ser Arg Leu Gln Leu Leu Gly Ala Thr Cys Met Phe Val Ala Ser Lys
            100                 105                 110

Met Lys Glu Thr Ile Pro Leu Thr Ala Glu Lys Leu Cys Ile Tyr Thr
        115                 120                 125

Asp Asn Ser Ile Arg Pro Glu Glu Leu Leu Gln Met Glu Leu Leu Leu
    130                 135                 140

Val Asn Lys Leu Lys Trp Asn Leu Ala Ala Met Thr Pro His Asp Phe
145                 150                 155                 160

Ile Glu His Phe Leu Ser Lys Met Pro Glu Ala Glu Glu Asn Lys Gln
                165                 170                 175

Ile Ile Arg Lys His Ala Gln Thr Phe Val Ala Leu Cys Ala Thr Asp
            180                 185                 190

Val Lys Phe Ile Ser Asn Pro Pro Ser Met Val Ala Ala Gly Ser Val
        195                 200                 205

Val Ala Ala Val Gln Gly Leu Asn Leu Arg Ser Pro Asn Asn Phe Leu
    210                 215                 220

Ser Tyr Tyr Arg Leu Thr Arg Phe Leu Ser Arg Val Ile Lys Cys Asp
225                 230                 235                 240

Pro Asp Cys Leu Arg Ala Cys Gln Glu Gln Ile Glu Ala Leu Leu Glu
                245                 250                 255

Ser Ser Leu Arg Gln Ala Gln Gln Asn Met Asp Pro Lys Ala Ala Glu
            260                 265                 270

```
Glu Glu Glu Glu Glu Glu Glu Val Asp Leu Ala Cys Thr Pro Thr
            275                 280                 285
Asp Val Arg Asp Val Asp Ile
        290             295
```

CANCER THERAPY BASED ON TUMOR ASSOCIATED ANTIGENS DERIVED FROM CYCLIN D1

CROSS REFERENCE TO RELATED APPLICATIONS

This application claims priority to Great Britain Patent Application Number GB1009222.9, filed on Jun. 2, 2010, and U.S. Provisional Patent Application No. 61/350,731, filed on Jun. 2, 2010, and this application is also related to PCT/EP2011/059121 entitled "Improved cancer therapy based on tumor associated antigens derived from cyclin D1", the entire contents of which are all the above mentioned documents are hereby incorporated by reference in their entireties.

BACKGROUND OF THE INVENTION

1. Field of the Invention

The present invention relates to cyclin-derived peptides for use in the improved treatment of cancer in a patient, particularly in the form of a combination therapy using a vaccine. Other aspects relate to the use of the peptides or a combination thereof as a diagnostic tool.

2. Background of the Invention

Stimulation of an immune response is dependent upon the presence of antigens recognized as foreign by the host immune system. The discovery of the existence of tumor associated antigens has now raised the possibility of using a host's immune system to intervene in tumor growth. Various mechanisms of harnessing both the humoral and cellular arms of the immune system are currently being explored for cancer immunotherapy.

Certain elements of the cellular immune response are capable of specifically recognizing and destroying tumor cells. The isolation of cytotoxic T-cells (CTL) from tumor-infiltrating cell populations or from peripheral blood suggests that these cells play an important role in natural immune defenses against cancer (Cheever et al., Annals N.Y. Acad. Sci. 1993 690:101-112; Zeh H J, Perry-Lalley D, Dudley M E, Rosenberg S A, Yang J C; J. Immunol. 1999, 162(2):989-94; High avidity CTLs for two self-antigens demonstrate superior in vitro and in vivo antitumor efficacy.). CD8-positive T-cells (TCD8+) in particular, which recognize Class I molecules of the major histocompatibility complex (MHC)-bearing peptides of usually 8 to 10 amino acid residues derived from proteins or defective ribosomal products (DRiPS) (Schubert U, Anton L C, Gibbs J, Norbury C C, Yewdell J W, Bennink J R.; Rapid degradation of a large fraction of newly synthesized proteins by proteasomes; Nature 2000; 404(6779):770-774) located in the cytosol, play an important role in this response. The MHC-molecules of the human are also designated as human leukocyte-antigens (HLA).

There are two classes of MHC-molecules: MHC class I molecules that can be found on most cells having a nucleus which present peptides that result from proteolytic cleavage of endogenous proteins, DRIPS, and larger peptides. MHC class II molecules can be found predominantly on professional antigen presenting cells (APCs), and present peptides of exogenous proteins that are taken up by APCs during the course of endocytosis, and are subsequently processed (Cresswell P. Annu Rev. Immunol. 1994; 12:259-93). Complexes of peptide and MHC class I molecules are recognized by CD8-positive cytotoxic T-lymphocytes bearing the appropriate TCR, complexes of peptide and MHC class II molecules are recognized by CD4-positive-helper-T-cells bearing the appropriate TCR. It is well known that the TCR, the peptide and the MHC are thereby abundant in a stoichiometric amount of 1:1:1.

CD4-positive helper T-cells play an important role in orchestrating the effector functions of anti-tumor T-cell responses and for this reason the identification of CD4-positive T-cell epitopes derived from tumor associated antigens (TAA) may be of great importance for the development of pharmaceutical products for triggering anti-tumor immune responses (Kobayashi, H., R. Omiya, M. Ruiz, E. Huarte, P. Sarobe, J. J. Lasarte, M. Herraiz, B. Sangro, J. Prieto, F. Borras-Cuesta, and E. Celis. 2002. Identification of an antigenic epitope for helper T lymphocytes from carcinoembryonic antigen. Clin. Cancer Res. 8:3219-3225., Gnjatic, S., D. Atanackovic, E. Jager, M. Matsuo, A. Selvakumar, N. K. Altorki, R. G. Maki, B. Dupont, G. Ritter, Y. T. Chen, A. Knuth, and L. J. Old. 2003. Survey of naturally occurring CD4+ T-cell responses against NY-ESO-1 in cancer patients: Correlation with antibody responses. Proc. Natl. Acad. Sci. U.S.A. 100(15):8862-7) CD4+ T cells can lead to locally increased levels of IFNγ (Qin Z, Schwartzkopff J, Pradera F, Kammertoens T, Seliger B, Pircher H, Blankenstein T; A critical requirement of interferon gamma-mediated angiostasis for tumor rejection by CD8+ T cells; Cancer Res. 2003 J; 63(14):4095-4100).

In the absence of inflammation, expression of MHC class II molecules is mainly restricted to cells of the immune system, especially professional antigen-presenting cells (APC), e.g., monocytes, monocyte-derived cells, macrophages, dendritic cells. In tumor patients, cells of the tumor have surprisingly been found to express MHC class II molecules (Dengjel J, Nastke M D, Gouttefangeas C, Gitsioudis G, Schoor O, Altenberend F, Müller M, Krämer B, Missiou A, Sauter M, Hennenlotter J, Wernet D, Stenzl A, Rammensee H G, Klingel K, Stevanović S.; Unexpected abundance of HLA class II presented peptides in primary renal cell carcinomas; Clin Cancer Res. 2006; 12:4163-4170).

Since the constitutive expression of HLA class II molecules is usually limited to cells of the immune system (Mach, B., V. Steimle, E. Martinez-Soria, and W. Reith. 1996. Regulation of MHC class II genes: lessons from a disease. Annu Rev. Immunol. 14:301-331), the possibility of isolating class II peptides directly from primary tumors was not considered possible. However, Dengjel et al. were recently successful in identifying a number of MHC Class II epitopes directly from tumors (EP 04 023 546.7, EP 05 019 254.1; Dengjel J, Nastke M D, Gouttefangeas C, Gitsioudis G, Schoor O, Altenberend F, Müller M, Krämer B, Missiou A, Sauter M, Hennenlotter J, Wernet D, Stenzl A, Rammensee HG, Klingel K, Stevanović S.; Unexpected abundance of HLA class II presented peptides in primary renal cell carcinomas; Clin Cancer Res. 2006; 12:4163-4170).

For a peptide to trigger (elicit) a cellular immune response, it must bind to an MHC-molecule. This process is dependent on the allele of the MHC-molecule and of the amino acid sequence of the peptide. MHC-class-1-binding peptides are usually 8-10 amino acid residues in length and usually contain two conserved residues ("anchors") in their sequence that interact with the corresponding binding groove of the MHC-molecule. In this way each MHC allele has a "binding motif" determining which peptides can bind specifically to the binding groove (Rammensee H. G., Bachmann J. and Stevanovic, S; MHC Ligands and Peptide Motifs, Chapman & Hall 1998).

In the MHC class I dependent immune reaction, peptides not only have to be able to bind to certain MHC class I molecules expressed by tumor cells, they also have to be recognized by T-cells bearing specific T-cell receptors (TCR).

The antigens that are recognized by the tumor specific cytotoxic T-lymphocytes, that is, their epitopes, can be molecules derived from all protein classes, such as enzymes, receptors, transcription factors, etc. which are up-regulated in cells of the respective tumor. Furthermore, tumor associated antigens, for example, can also be unique to tumor cells, for example as products of mutated genes or from alternative open reading frames (ORFs), or from protein splicing (Vigneron N, Stroobant V, Chapiro J, Ooms A, Degiovanni G, Morel S, van der Bruggen P, Boon T, Van den Eynde B J. An antigenic peptide produced by peptide splicing in the proteasome, Science 2004 Apr. 23; 304 (5670):587-90.). Another important class of tumor associated antigens are tissue-specific antigens, such as CT ("cancer testis")-antigens that are expressed in different kinds of tumors and in healthy tissue of the testis. Basically, any peptide able to bind a MHC molecule may function as a T-cell epitope. A prerequisite for the induction of an in vitro or in vivo T-cell-response is the presence of a T-cell with a corresponding TCR and the absence of immunological tolerance for this particular epitope.

Therefore, TAAs are a starting point for the development of a tumor vaccine. The methods for identifying and characterizing the TAAs are based on the use of CTL that can be isolated from patients or healthy subjects, or they are based on the generation of differential transcription profiles or differential peptide expression patterns between tumors and normal tissues (Lemmel C., Weik S., Eberle U., Dengjel J., Kratt T., Becker H. D., Rammensee H. G., Stevanovic S, Nat. Biotechnol. 2004 April; 22(4):450-4, T. Weinschenk, C. Gouttefangeas, M. Schirle, F. Obermayr, S. Walter, O, Schoor, R. Kurek, W. Loeser, K. H. Bichler, D. Wernet, S. Stevanovic, and H. G. Rammensee. Integrated functional genomics approach for the design of patient-individual anti-tumor vaccines. Cancer Res. 62 (20):5818-5827, 2002.).

However, the identification of genes overexpressed in tumor tissues or human tumor cell lines, or selectively expressed in such tissues or cell lines, does not provide precise information as to the use of the antigens transcribed from these genes in an immune therapy. This is because only an individual subpopulation of epitopes of these antigens are suitable for such an application since a T-cell with a corresponding TCR has to be present and immunological tolerance for this particular epitope needs to be absent or minimal. It is therefore important to select only those peptides from overexpressed or selectively expressed proteins that are presented in connection with MHC molecules against which a functional T-cell can be found. Such a functional T-cell is defined as a T-cell that upon stimulation with a specific antigen can be clonally expanded and is able to execute effector functions ("effector T-cell").

T-helper cells play an important role in orchestrating the effector function of CTLs in anti-tumor immunity. T-helper cell epitopes that trigger a T-helper cell response of the TH1 type support effector functions of CD8-positive killer T-cells, which include cytotoxic functions directed against tumor cells displaying tumor-associated peptide/MHC complexes on their cell surfaces. In this way tumor-associated T-helper cell epitopes, alone or in combination with other tumor-associated peptides, can serve as active pharmaceutical ingredients of vaccine compositions which stimulate anti-tumor immune responses.

Since both types of response, CD8 and CD4 dependent, contribute jointly and synergistically to the anti-tumor effect, the identification and characterization of tumor-associated antigens recognized by either CD8+ CTLs (ligand: MHC class I molecule+peptide epitope) or by CD4-positive CTLs (ligand: MHC class II molecule+peptide epitope) is important in the development of tumor vaccines.

Cyclin D1 belongs to the highly conserved cyclin family, more specifically to the cyclin D subfamily (Lew D J, Dulic V, Reed S I (1991). Isolation of three novel human cyclins by rescue of G1 cyclin (Cln) function in yeast. Cell 66, 1197-1206; Xiong Y, Connolly T, Futcher B, Beach D (1991). Human D-type cyclin. Cell 65, 691-699). Cyclins function as regulators of cyclin-dependent kinases (CDKs). Different cyclins exhibit distinct expression and degradation patterns which contribute to the temporal coordination of each event in cell cycle (Deshpande A, Sicinski P, Hinds P W (2005). Cyclins and cdks in development and cancer: a perspective. Oncogene 24, 2909-2915.) Cyclin D1 forms a complex with and functions as a regulatory subunit of CDK4 or CDK6, whose activity is required for cell cycle G1/S transition. CCND1 forms a serine/threonine kinase holoenzyme complex with CDK4 and CDK6 imparting substrate specificity to the complex (Bates S, Bonetta L, MacAllan D, Parry D, Holder A, Dickson C, Peters G (1994). CDK6 (PLSTIRE) and CDK4 (PSK-J3) are a distinct subset of the cyclin-dependent kinases that associate with cyclin D1. Oncogene 9, 71-79). Mutations, amplifications and overexpression of this gene, which alters cell cycle progression, are observed frequently in a variety of tumors and may contribute to tumorigenesis (Hedberg Y, Davoodi E, Roos G, Ljungberg B, Landberg G (1999). Cyclin-D1 expression in human renal-cell carcinoma. Int. J. Cancer 84, 268-272; Vasef M A, Brynes R K, Sturm M, Bromley C, Robinson R A (1999). Expression of cyclin D1 in parathyroid carcinomas, adenomas, and hyperplasias: a paraffin immunohistochemical study. Mod. Pathol. 12, 412-416; Troussard X, vet-Loiseau H, Macro M, Mellerin M P, Malet M, Roussel M, Sola B (2000). Cyclin D1 expression in patients with multiple myeloma. Hematol. J. 1, 181-185). Cyclin D1 is overexpressed in colorectal, gastric, esophageal, lung, kidney and breast cancer, as well as leukemia and lymphoma, with little expression in normal tissue. It is also typically overexpressed in mantle cell lymphoma, which is characterized by a t(11;14)(q13;q32) translocation that juxtaposes the protooncogene CCND1 at chromosome 11q13 to the Ig heavy chain gene at chromosome 14q32 (Wang et al., 2009; Kondo et al., 2008).

A common A/G single nucleotide polymorphism (A870G) results in two distinct mRNA isoforms a and b in cyclin D1. The alternately spliced isoform b encodes a truncated protein which has been linked to higher incidence of tumor onset including sporadic RCC, lung cancer, colon cancer, and other cancer types (Fu M, Wang C, LI Z, Sakamaki T, Pestell R G (2004). Minireview: Cyclin D1: normal and abnormal functions. Endocrinology 145, 5439-5447; Yu J, Habuchi T, Tsuchiya N, Nakamura E, Kakinuma H, Horikawa Y, Inoue T, Ogawa O, Kato T (2004). Association of the cyclin D1 gene G870A polymorphism with susceptibility to sporadic renal cell carcinoma. J Urol. 172, 2410-2413). Enhanced CCND1 expression has been linked to higher tumor grades, metastasis, and decreased survival (Maeda K, Chung Y, Kang S, Ogawa M, Onoda N, Nishiguchi Y, Ikehara T, Nakata B, Okuno M, Sowa M (1998). Cyclin D1 overexpression and prognosis in colorectal adenocarcinoma. Oncology 55, 145-151; McKay J A, Douglas J J, Ross V G, Curran S, Murray G I, Cassidy J, McLeod H L (2000). Cyclin D1 protein expression and gene polymorphism in colorectal cancer. Aberdeen Colorectal Initiative. Int. J. Cancer 88, 77-81; Bahnassy A A, Zekri A R, El-Houssini S, El-Shehaby A M, Mahmoud M R, Abdallah S, El-Serafi M (2004). Cyclin A and cyclin D1 as significant prognostic markers in colorectal cancer patients. BMC. Gastroenterol. 4, 22; Balcerczak E, Pasz-Walczak G, Kumor P, Panczyk M, Kordek R, Wierzbicki R, Mirowski M (2005). Cyclin D1 protein and CCND1 gene expression in colorectal cancer. Eur. J. Surg. Oncol. 31, 721-726).

For colorectal cancer, overexpression of CCND1 at the mRNA and protein levels has been described frequently. This can be explained by the well-established fact that CCND1 is a target gene of the β-Catenin-TCF/LEF pathway which is frequently upregulated in colorectal carcinoma (Shtutman M, Zhurinsky J, Simcha I, Albanese C, D'Amico M, Pestell R, Ben-Ze'ev A (1999). The cyclin D1 gene is a target of the beta-catenin/LEF-1 pathway. Proc. Natl. Acad. Sci. U.S. A 96, 5522-5527; Tetsu O, McCormick F (1999). Beta-catenin regulates expression of cyclin D1 in colon carcinoma cells. Nature 398, 422-426).

The cyclin peptide CCN-001 (LLGATCMFV) (SEQ ID NO: 1) was identified by Sadovnikova and colleagues (Sadovnikova E, Jopling L A, Soo K S, Stauss H J (1998). Generation of human tumor-reactive cytotoxic T cells against peptides presented by non-self HLA class I molecules. Eur. J. Immunol. 28, 193-200). After induction of allo-restricted T cells (i.e. of HLA-A2-negative donors) against several Cyclin D1-derived HLA-A*02-binding peptides, it has been shown that T cell clones recognizing CCN-001 could lyse HLA-A*02 positive tumor cells endogenously expressing Cyclin D1 but not HLA-A*02 positive cells negative for Cyclin D1. Thus it was shown that CCN-001 is naturally processed and presented only by indirect evidence.

For some time it had been suggested that T cells recognizing cyclin D1-derived epitopes were absent from the T cell repertoire because of the thymic expression of cyclin D1. Assuming this, the generation of autologous CTL to cyclin D1 would have been impossible.

However, Kondo et al. (Kondo E, Maecker B, Weihrauch M R, Wickenhauser C, Zeng W, Nadler L M, Schultze J L, von Bergwelt-Baildon M S (2008). Cyclin D1-specific cytotoxic T lymphocytes are present in the repertoire of cancer patients: implications for cancer immunotherapy. Clin Cancer Res 14, 6574-6579) showed that CTL specific for the epitope CCN-001 (LLGATCMFV) could be generated from HLA-A2+ donors as well. They demonstrated this for healthy donors as well as for colon cancer patients and mantle cell lymphoma patients. As APCs, they used autologous CD40-activated B cells.

Wang et al. (Wang M, Sun L, Qian J, Han X, Zhang L, Lin P, Cai Z, Yi Q (2009). Cyclin D1 as a universally expressed mantle cell lymphoma-associated tumor antigen for immunotherapy. Leukemia 23, 1320-1328) generated cyclin D1-specific CTL against CCN-001 using T cells from mantle cell lymphoma patients and autologous mature monocyte-derived DCs as APCs. They did not use the original peptide, but a heteroclitic peptide where the first amino acid (L) was replaced by Y, enhancing the MHC binding. Resulting CTLs could kill cyclin D1+ expressing cells, including primary lymphoma cells from HLA-A2+ mantle cell lymphoma patients. The peptide was also used in other studies (Kondo E, Gryschok L, Klein-Gonzalez N, Rademacher S, Weihrauch M R, Liebig T, Shimabukuro-Vornhagen A, Kochanek M, Draube A, von Bergwelt-Baildon MS (2009a). CD40-activated B cells can be generated in high number and purity in cancer patients: analysis of immunogenicity and homing potential. Clin Exp. Immunol. 155, 249-256; Kondo E, Gryschok L, Schultze J L, von Bergwelt-Baildon M S (2009b). Using CD40-activated B cells to efficiently identify epitopes of tumor antigens. J Immunother. 32, 157-160) to demonstrate the usefulness of CD40-activated B cells as APCs. Buchner et al (in Buchner et al. Phase 1 Trial of Allogeneic Gene-Modified Tumor Cell Vaccine RCC-26/CD80/IL-2 in Patients with Metastatic Renal Cell Carcinoma. Human Gene Therapy. Mar. 2010, 21(3): 285-297) mention the CCN-001 peptide in a clinical study.

WO 2005/035714 describes vaccines for treating or preventing cancer, comprising tumor-associated HLA-restricted antigens, and in particular HLA-A2 restricted antigens. In specific aspects, cyclin D peptides are provided. Such peptides can be used to elicit specific CTLs that preferentially attack tumor cells. The cyclin D peptide may comprise the sequence LLGATCMFV, or a fragment thereof. Further described is a method for treating or prevent-ing a cancer in a patient comprising administering to the patient a therapeutically effective amount of a vaccine comprising a peptide. The method may further comprise treating the patient with a second anticancer agent, wherein the second anticancer agent is selected from a long list of agents, such as chemotherapeutic agents, such as, for example cyclophosphamide. The second anticancer agent may be administered simultaneously with the vaccine, or administered at a different time than the vaccine. Nevertheless, WO 2005/035714 does not describe any advantages regarding a combination treatment using cyclin D1 peptides.

In view of the above, very little is known about an effective use of cyclin D1 derived peptides in an effective immunotherapy against cancer. It is therefore an object of the present invention, to provide novel approaches for a more effective immunotherapeutic treatment of cancer, based on cyclin D1 derived peptides.

SUMMARY OF THE INVENTION

In a first aspect thereof, the object of the present invention is solved by a peptide consisting of or essentially consisting of an amino acid sequence selected from SEQ ID NO: 1 to SEQ ID NO: 18 for use in the treatment of cancer in a patient, or a combination comprising at least one peptide consisting of or essentially consisting of an amino acid sequence selected from SEQ ID NO: 1 to SEQ ID NO: 18 for use in the treatment of cancer in a patient.

According to the present invention, the cancer can be selected from the group of lung cancer, head and neck cancer, breast cancer, pancreatic cancer, prostate cancer, renal cancer, esophageal cancer, bone cancer, testicular cancer, cervical cancer, gastrointestinal cancer, glioblastoma, leukemia, lymphomas, mantle cell lymphoma, pre-neoplastic lesions in the lung, colon cancer, melanoma, bladder cancer and any other neoplastic diseases. Preferred are renal cancer, colon cancer, and glioblastoma.

BRIEF DESCRIPTION OF THE FIGURES

FIG. 1 shows the amino acid sequence of cyclin D1 according to SEQ ID NO: 27, with the positions of the tumor associated peptides as used in the present invention indicated in bold.

DETAILED DESCRIPTION OF THE INVENTION

Figure 2A:
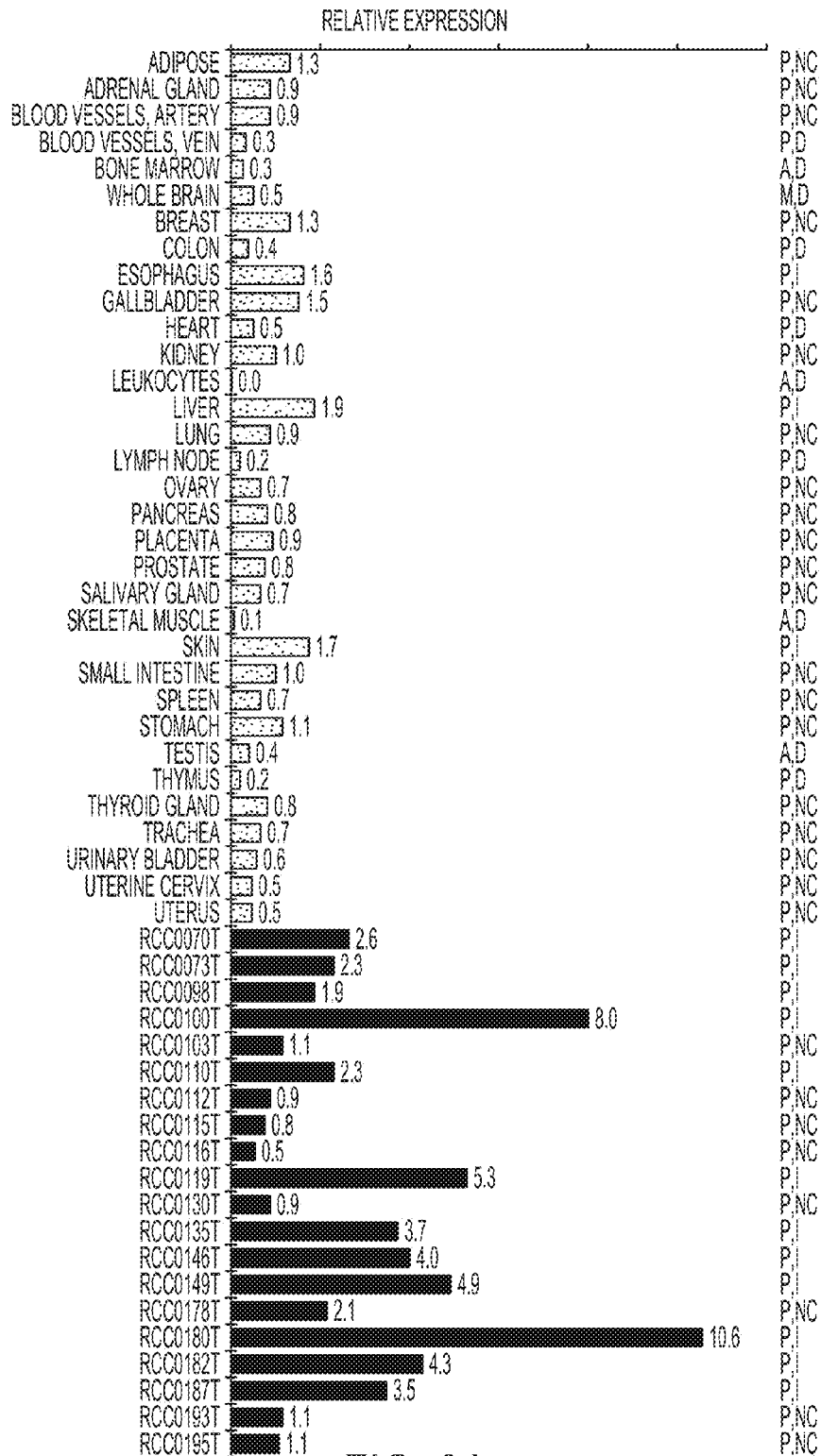
FIG. 2 shows the average overexpression of CCND1 in renal cancer cells (ccRCC) against the average expression in normal tissues (FIG. 2A) as 3.0-fold (expression data from dataset 1), and separately analyzed 5.7-fold in primary tumors and 5.4-fold in metastases (FIG. 2B, expression data from independent dataset 2). 60% of primary tumors showed an overexpression against normal kidney (FIG. 2A, black bars with an "I" from "increased" above the bar).
Figure 2B:
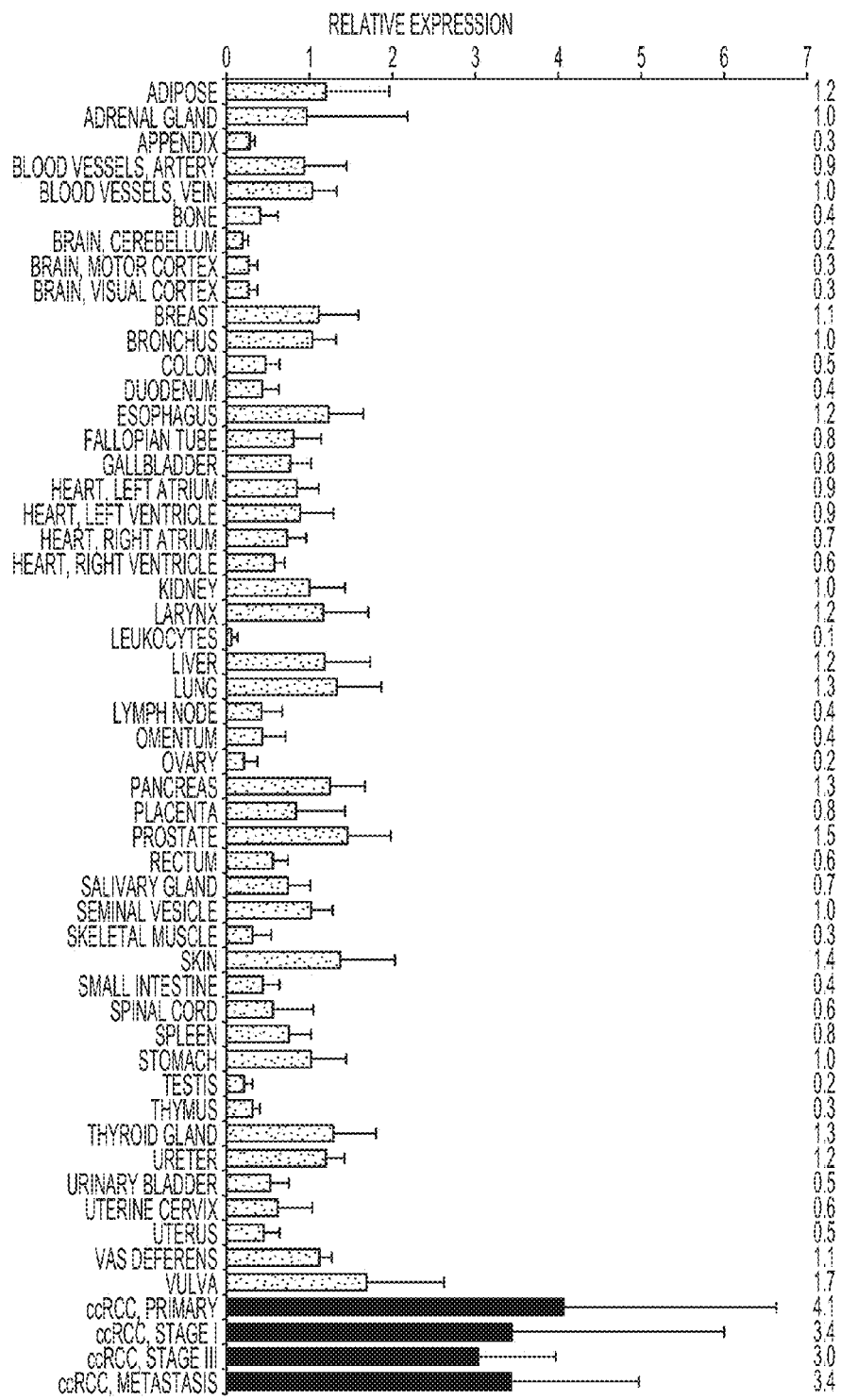
Figure 3A:
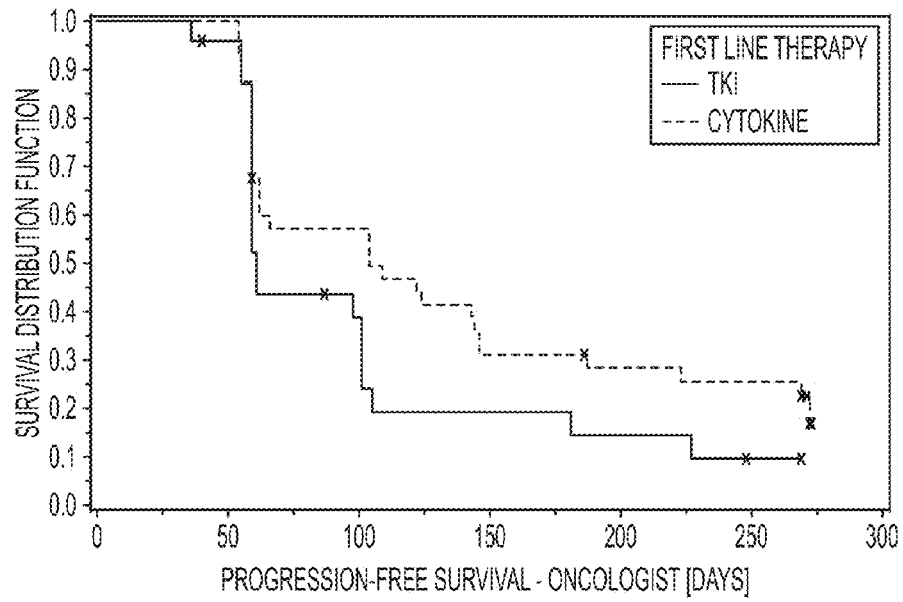
FIG. 3 shows the better PFS (A) and overall survival (OS) (B) in IMA901-vaccinated patients with prior cytokine therapy (dashed lines), compared to patients with prior TKI therapy (solid lines).
Figure 3B:
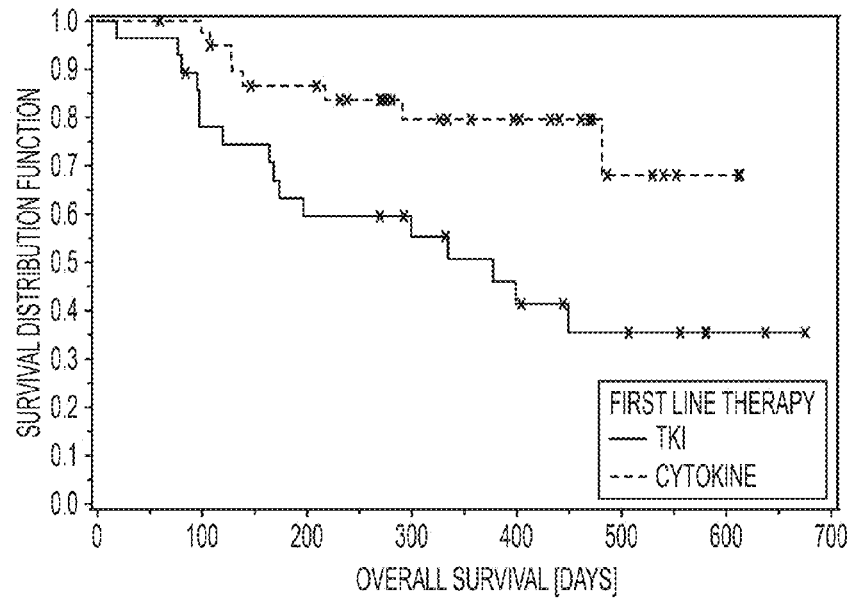
Figure 4A:
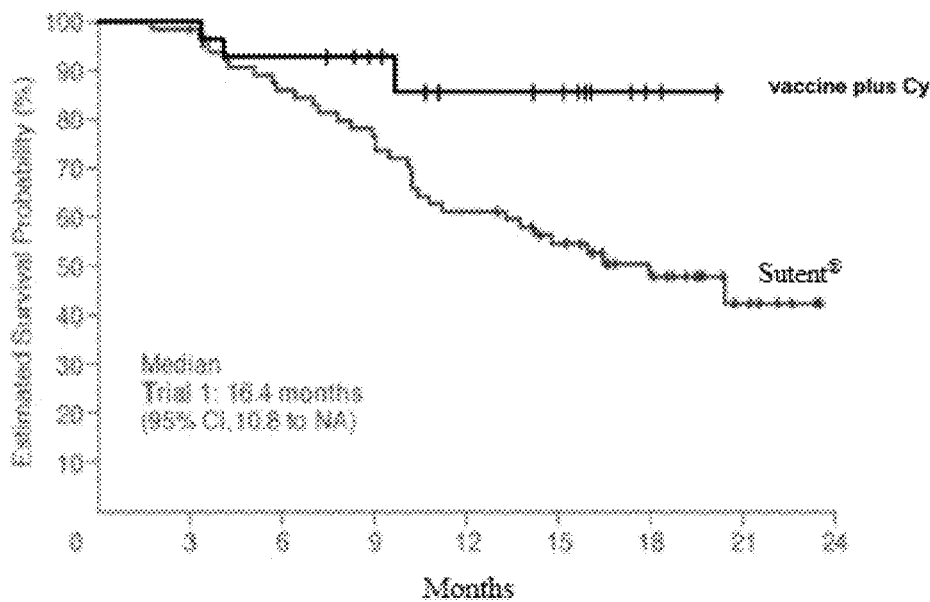
FIG. 4 shows the overall survival (OS) of the CCN-001 containing vaccine IMA901 (as described, for example, in EP1760089, herewith incorporated by reference) versus Sutent® (A) and versus Nexavar® (B) as 2nd line post cytokine treatment.
Figure 4B:
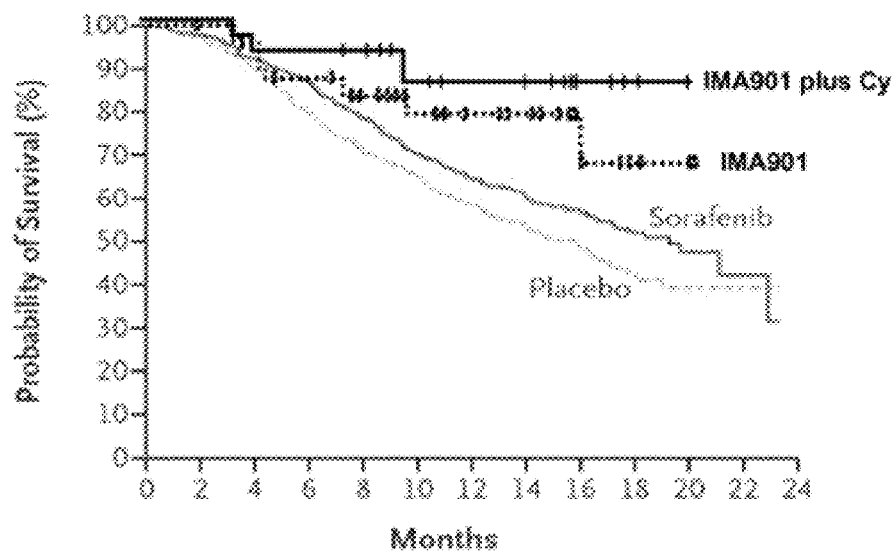
Figure 5A:
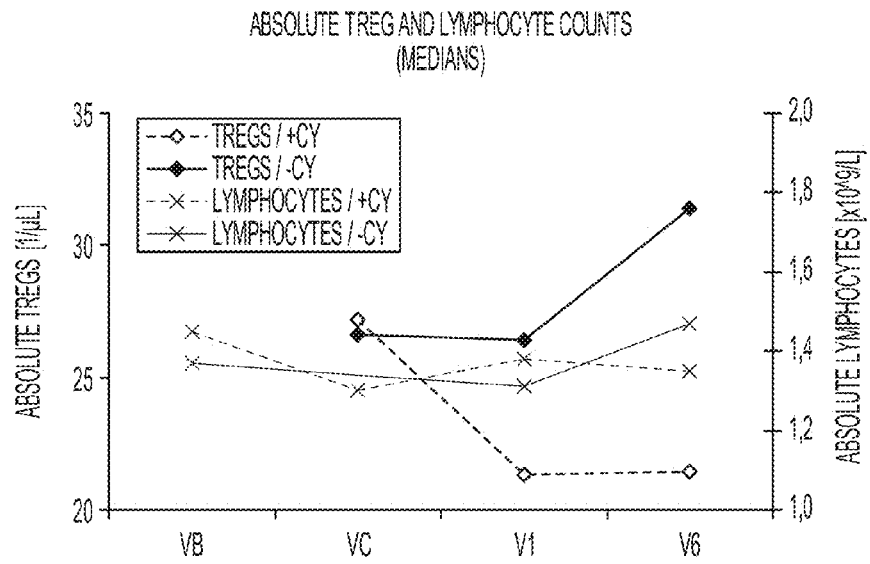
FIG. 5 shows reduction of regulatory T cells in the patient group pretreated with cyclophosphamide (+CY). Absolute counts are shown in (A), percent change from baseline is shown in (B).
Figure 5B:
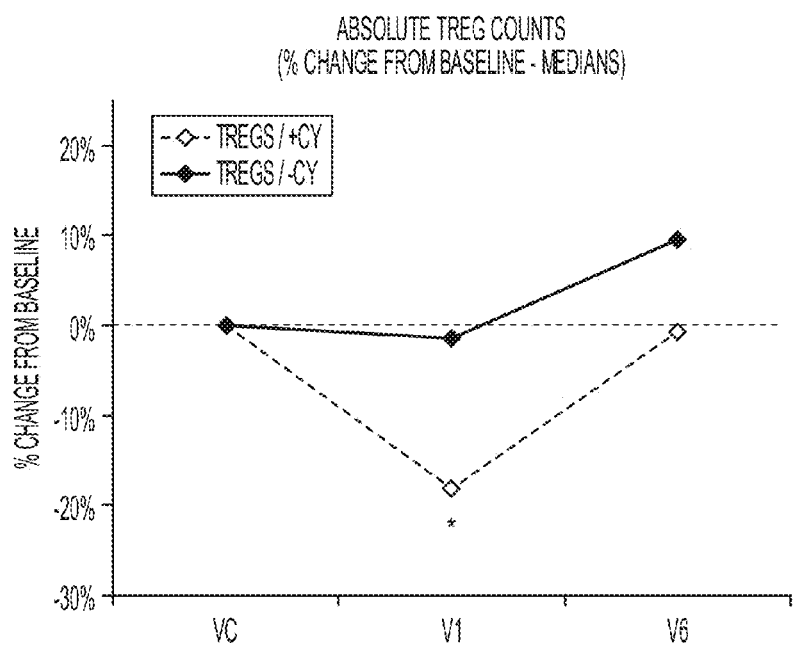
Figure 6A:
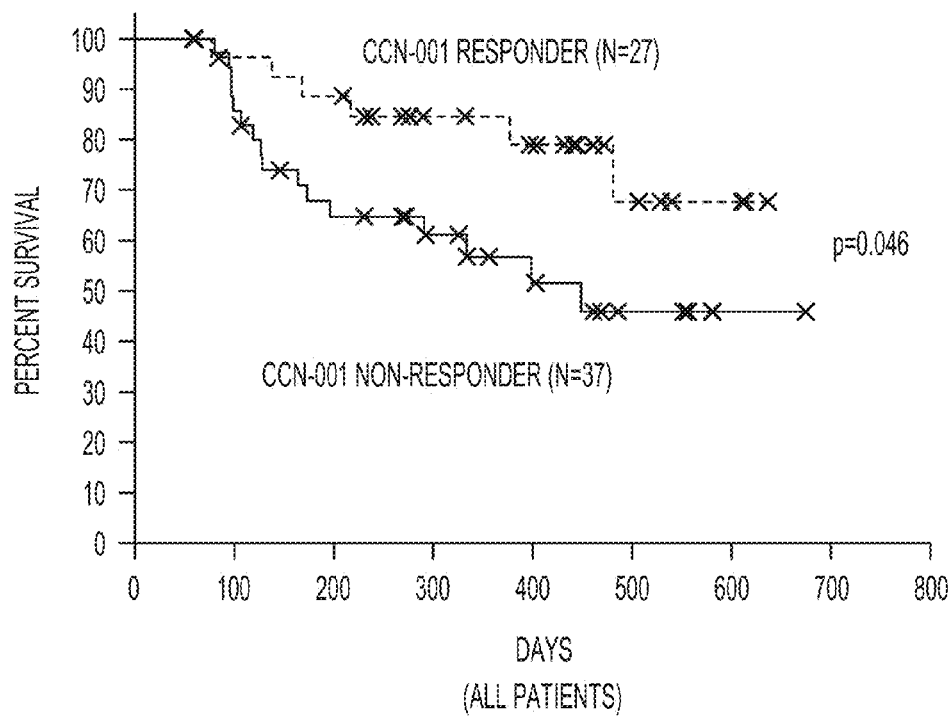
FIG. 6 shows that patients responding against CCN-001 survive significantly longer than non-CCN-001-responding patients (A). This favorable effect of T cell response against CCN-001 was even more evident within the patient group pretreated with cyclophosphamide (B).
Figure 6B:
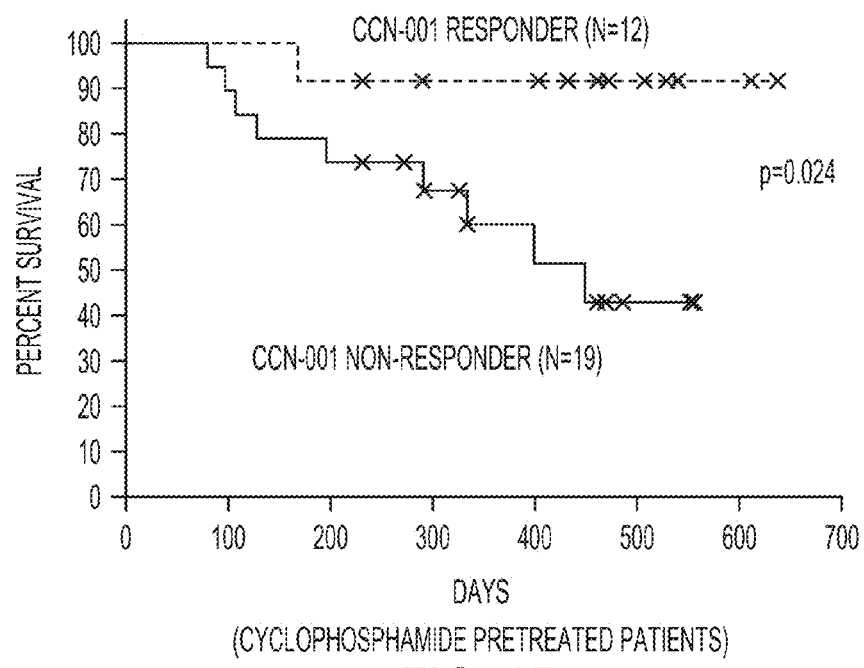
Figure 7A:
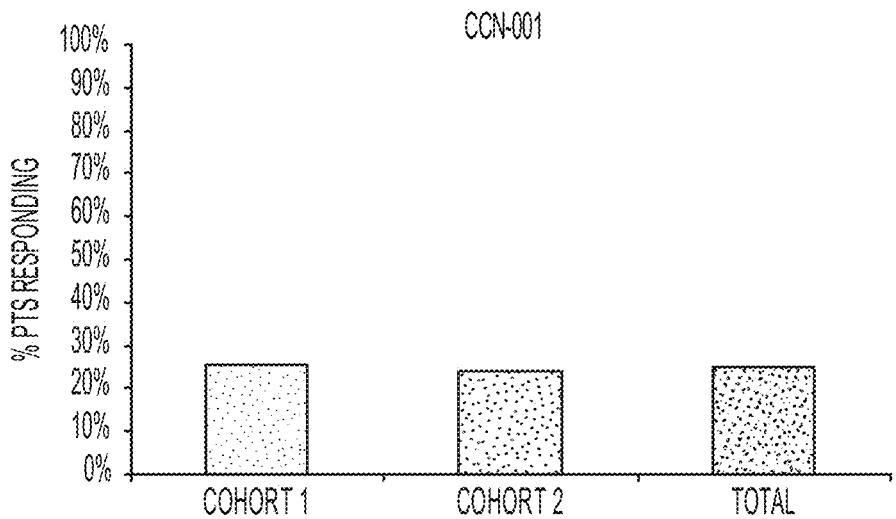
FIG. 7 shows vaccine induced responses to CCN-001. Patients were immunized at various time points with IMA910 peptide-cocktail (as described, for example, in WO2009/015841, herewith incorporated by reference) in the presence of GM-CSF (Cohort 1) or GM-CSF+ Imiquimod (Cohort 2). Immune responses to HLA-A*0201 binding peptides were investigated within immuno-monitoring analyses by multimer assay. Subsequently, PBMCs of patients were in vitro sensitized and analyzed by flow cytometric analysis and multimer staining A) Immune responder rate to CCN-001 of all (black) patients or patients treated without (light grey) and with (dark grey) imiquimod. Bars indicate the frequency of patients with a vaccine induced responses to CCN-001 peptide. B) Immune response to CCN-001 of one representative patient before (left) and after vaccination (right).
Figure 7B:
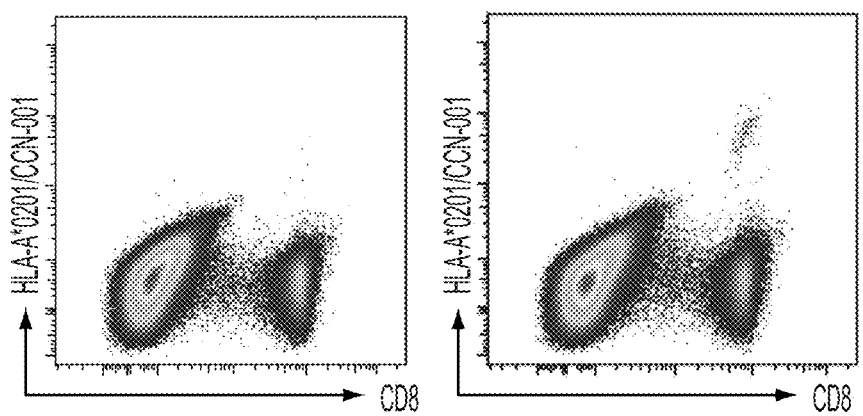

In the context of the present invention, preferred are peptides that consist of an amino acid sequence according to any of SEQ ID NO: 1 to SEQ ID NO: 18. "Consisting essentially of" shall mean that a peptide, in addition to the sequence according to any of SEQ ID NO: 1 to SEQ ID NO: 18 contains additional N- and/or C-terminally located stretches of amino acids that are not necessarily forming part of the peptide that functions as core sequence of the pep-tide comprising the binding motif and as an immunogenic T-helper epitope. Nevertheless, these stretches can be important in order to provide for an efficient introduction of the peptide into the cells.

The following table lists the cyclin D1-derived peptides as used in the context of the present invention.

TABLE 1

Peptides as used in the context of the present invention

| Peptide Name | Peptide Sequence | Position in Cyclin D1 (aa) | Binding to | SEQ ID NO: |
|---|---|---|---|---|
| CCN-001 | LLGATCMFV | 101-109 | HAL-1 HLA-A*02 | 1 |
| CCN-002 | RLTRFLSRV | 228-236 | HLA-1 HLA-A*02 | 2 |
| CCN-003 | NPPSMVAAGSVVAAV | 198-212 | HLA-II DRB1*0401 | 3 |
| CCN-004 | EVFPLAMNY | 76-84 | HLA-I HLA-A*26 | 4 |
| CCN-006 | ETIPLTAEKL | 115-124 | HLA-I HLA-A*02 HLA-A*68 | 5 |
| CCN-007 | ALLESSLRQA | 253-262 | HLA-I HLA-A*02 | 6 |
| CCN-A | IVATWMLEV | 59-67 | HLA-A*02 | 7 |
| CCN-B | SVVAAVQGL | 207-215 | HLA-A*02 | 8 |
| CCN-C | SVVAAVQVLNL | 207-217 | HLA-A*02 | 9 |
| CCN-D | NYLDRFLSL | 83-91 | HLA-A*24 | 10 |
| CCN-E | DRVLRAML | 25-32 | B*14 | 11 |
| CCN-F1 | EEEVFPLAM | 74-82 | B*1801 | 12 |
| CCN-F2 | EEVFPLAMNY | 75-84 | HLA-I | 13 |
| CCN-F3 | EVFPLAMNYL | 76-85 | HLA-I | 14 |
| CCN-G | NLRSPNNFLSY | 216-226 | HLA-I | 15 |
| CCN-H | VNKLKWNL | 145-152 | HLA-I | 16 |
| CCN-I | VQKEVLPSM | 48-56 | HLA-I | 17 |
| CCN-J | MPEAEENKQII | 168-178 | unclear | 18 |

In one embodiment of the present invention, the peptide as used in the present invention is a fusion protein and comprises the 80 N-terminal amino acids of the HLA-DR antigen-associated invariant chain (p33, in the following "Ii") as derived from the NCBI, GenBank Accession-number X00497 (Strubin, M., Mach, B. and Long, E. O. The complete sequence of the mRNA for the HLA-DR-associated invariant chain reveals a polypeptide with an unusual transmembrane polarity EMBO J. 3 (4), 869-872 (1984).

If a peptide as used in the present invention is larger than around 12 amino acid residues is used directly to bind to a MHC molecule, it is preferred that the residues that flank the core HLA binding region are ones that do not substantially affect the ability of the peptide to bind specifically to the binding groove of the MHC molecule or to present the peptide to the CTL. However, as already indicated above, it will be appreciated that larger peptides may be used, especially when encoded by a polynucleotide, since these larger peptides may be fragmented by suitable antigen-presenting cells.

Examples for peptides of MHC ligands, motifs, variants, as well as certain examples for N- and/or C-terminal extensions can be, for example, derived from the database SYFPEITHI (Rammensee H, Bachmann J, Emmerich N P, Bachor O A, Stevanovic S. SYFPEITHI: database for MHC ligands and peptide motifs. Immunogenetics. 1999 November; 50(3-4): 213-9) at http://syfpeithi.bmi-heidelberg.com/, and the references as cited therein. A preferred MHC class I specific peptide as used in the present invention exhibits an overall length of between 9 and 16, preferably between 9 and 12 amino acids. It shall be understood that those peptides might be used (for example in a vaccine) as longer peptides, similar to MHC class II peptides. Methods to identify MHC class I specific "Core sequences" having a certain HLA-specific amino acid motif for HLA class I-molecules are known to the person of skill and these sequences can be predicted, for example, by the computer programs PAProC (http://www.uni-tuebingen.de/uni/kxi/) and SYFPEITHI (http://www.syfpeithi.de).

By "peptide" the inventors include not only molecules in which amino acid residues are joined by peptide (—CO—NH—) linkages but also molecules in which the peptide bond is reversed. Such retro-inverso peptidomimetics may be made using methods known in the art, for example such as those described in Meziere et al (1997) J. Immunol. 159, 3230-3237, incorporated herein by reference. This approach involves making pseudopeptides containing changes involving the backbone, and not the orientation of side chains. Meziere et al (1997) show that, at least for MHC class II and T helper cell responses, these pseudopeptides are useful. Retro-inverse peptides, which contain NH—CO bonds instead of CO—NH peptide bonds, are much more resistant to proteolysis.

In a particularly preferred embodiment, the peptide as used in the present invention includes the amino acid sequence as indicated, and at least one further T-cell epitope wherein the further T-cell epitope is able to facilitate the production of a T-cell response directed at the type of tumor that aberrantly expresses a tumor-associated antigen. Thus, the peptides of the invention include so-called "beads on a string" polypeptides which can also be used as vaccines.

It will be appreciated from the following that in some applications the peptides as used in the present invention may be used directly (i.e. they are not produced by expression of a polynucleotide in a patient's cell or in a cell given to a patient); in such applications it is preferred that the peptide has fewer than 100 or 50 residues. A preferred peptide of the present invention exhibits an overall length of between 9 and 30 amino acids.

In the context of the present invention, a "combination" shall mean 2, 3, 4, 5, 6, 7, 8, 9, 10, 11, 12, 13, 14, 15, 16, 17 or 18 different peptides or even more peptides as used in the present invention. A suitable vaccine will preferably contain 4, 5, 6 or 7 different peptides, and most preferably 6 different peptides. A combination can also be dependent from the specific type of cancer that the patient to be treated is suffering from as well as the status of the disease, earlier treatment regimens, the immune status of the patient, and, of course, the HLA-genotype of the patient. Preferred combinations are selected from at least one of a peptide selected from SEQ ID NO: 1 to SEQ ID NO: 18 together with a non-cyclin-derived second tumor associated peptide, such as, for example, the ones in SEQ ID NO: 19 to SEQ ID NO: 26. A combination shall include the peptides both in separate or joint containers or dosage forms, which can be administered simultaneously or in separate dosages, as long as the peptides exhibit a combined effect, in particular a therapeutic effect, in the context of the treatment as described herein.

The peptides or combination as used in the present invention are particularly useful in immunotherapeutic methods to effectively target and kill cancer cells which express or aberrantly express cyclin D1.

Another important aspect of the present invention then relates to the peptide or combination as used according to the present invention, wherein said peptide or combination is administered in the form of an anti-cancer vaccine. Preferred is a vaccine comprising a (synthetic) peptide or peptides or a combination thereof as described above. The composition vaccine can also be dependent from the specific type of cancer that the patient to be treated is suffering from as well as the status of the disease, earlier treatment regimens, the immune status of the patient, and, of course, the HLA-genotype of the patient.

Preferred is a combination as used according to the present invention, which further comprises the administration of at least one additional tumor associated peptide which is not derived from cyclin D1, such as, for example, a peptide selected from any of SEQ ID NO: 19 to SEQ ID NO: 26 according to the following table 2.

TABLE 2

Peptides as used in the combination of the present invention

| Peptide Name | Peptide Sequence | Binding to | SEQ ID NO: |
|---|---|---|---|
| Met-001 | YVDPVITSI | HLA-A*02 | 19 |
| Muc-001 | STAPPVHNV | HLA-A*02 | 20 |
| Muc-002 | LLLLTVLTV | HLA-A*02 | 21 |
| CEA-004 | YLSGANLNL | HLA-A*02 | 22 |
| CEA-005 | YLSGADLNL | HLA-A*02 | 23 |
| CEA-006 | SPQYSWRINGIPQQHT | HLA-DR | 24 |
| TGFBI-001 | ALFVRLLALA | HLA-A*02 | 25 |
| BIR-002 | TLGEFLKLDRERAKN | HLA-DR | 26 |

Preferred is a combination as used according to the present invention, wherein said at least one additional tumor associated peptide is chosen based on its ability to bind to a different HLA-molecule, compared to the other peptides as present in said combination.

In view of the above, preferred combinations as used in the present invention are selected from one of the following: A combination comprising SEQ ID NO: 1 and SEQ ID NO: 19; or SEQ ID NO: 1 and SEQ ID NO: 20; or SEQ ID NO: 1, SEQ ID NO: 19, and SEQ ID NO: 20; a combination comprising SEQ ID NO: 1, a peptide selected from SEQ ID NO: 22; SEQ ID NO: 23, and SEQ ID NO: 24; a combination comprising SEQ ID NO: 1, a peptide selected from SEQ ID NO: 22; SEQ ID NO: 23, and SEQ ID NO: 24; and SEQ ID NO: 25; a combination comprising SEQ ID NO: 1, a peptide selected from SEQ ID NO: 22; SEQ ID NO: 23, and SEQ ID NO: 24; and SEQ ID NO: 19; a combination comprising SEQ ID NO: 1, and at least one peptide selected from SEQ ID NO: 2 to SEQ ID NO: 14; and a combination comprising SEQ ID NO: 1 and SEQ ID NO: 26.

The invention also provides a combination comprising SEQ ID NO: 6, and at least one peptide selected from SEQ ID NO: 1 to 5, and 7 to 14; and a combination comprising SEQ ID NO: 5, and at least one peptide selected from SEQ ID NO: 1 to 4 and SEQ ID NO: 6 to 14.

The invention also provides a combination as above which consists of the peptides as indicated.

The peptide or combination as used according to the present invention preferably constitutes a tumor or cancer vaccine. It may be administered directly into the patient, into the affected organ or systemically, or applied ex vivo to cells derived from the patient or a human cell line which are subsequently administered to the patient, or used in vitro to select a subpopulation from immune cells derived from the patient, which are then re-administered to the patient. The peptide may be substantially pure, or combined with an immune-stimulating adjuvant such as Detox, or used in combination with immune-stimulatory cytokines, or be administered with a suitable delivery system, for example liposomes. The peptide may also be conjugated to a suitable carrier such as keyhole limpet hemocyanin (KLH) or mannan (see WO 95/18145 and Longenecker et al (1993) Ann. NY Acad. Sci. 690, 276-291). The peptide may also be tagged, or be a fusion protein, or be a hybrid molecule.

Some of the peptides whose sequences are given in the present invention are expected to stimulate CD8 CTL. However, stimulation is more efficient in the presence of help provided by CD4-positive T-cells. Thus, the fusion partner or sections of a hybrid molecule suitably provide epitopes which stimulate CD4-positive T-cells. CD4-positive T cell stimulating epitopes are well known in the art and include those identified in tetanus toxoid.

The peptide for use in a cancer vaccine may be any suitable peptide. In particular, it may be a suitable 9-mer peptide or a suitable 7-mer or 8-mer or 10-mer or 11-mer peptide or 12-mer. Longer peptides may also be suitable, but 9-mer or 10-mer peptides as described in Table 1 as herein are preferred for HLA-class I peptides.

The peptides may be given intramuscularly, intradermally, intraperitoneally, intravenously or subcutaneously. It is preferred if the vaccine is administered into the muscle. It is also preferred if the vaccine is administered into the skin, i.e. intradermally. A further aspect of the invention provides a peptide as used in the present invention for intravenous (i.v.) injection, subcutaneous (s.c.) injection, intradermal (i.d.) injection, intraperitoneal (i.p.) injection, intramuscular (i.m.) injection. Preferred ways of peptide injection are s.c., i.d., i.p., i.m., and i.v. Doses of between 100 µg and 100 mg of peptide or DNA may be given, preferred is a range between 200 µg and 800 µg, even more preferred is a range between 200 µg and 600 µg and even more preferred a range between 400 µg and 500 µg and most preferred about 413 µg.

The peptide vaccine may be administered without adjuvant. Preferably, the peptides as active pharmaceutical components are given in combination with an adjuvant, such as, for example, IL-2, IL-12, GM-CSF, or complete Freund's adjuvant. The most preferred adjuvants can be found in, for example, Brinkman J A, Fausch S C, Weber J S, Kast W M. Peptide-based vaccines for cancer immunotherapy. Expert Opin Biol Ther. 2004 February; 4(2):181-98. The peptide vaccine may also be administered with an adjuvant such as BCG or alum. Other suitable adjuvants include Aquila's QS21 stimulon (Aquila Biotech, Worcester, Ma., USA) which is derived from saponin, mycobacterial extracts and synthetic bacterial cell wall mimics, and proprietary adjuvants such as Ribi's Detox. Quil A, another saponin derived adjuvant, may also be used (Superfos, Denmark). Other adjuvants such as CpG oligonucleotides, stabilized RNA, Imiquimod (commercially available under the trade name Aldara® from 3M Pharma, U.S.A.), Incomplete Freund's Adjuvant (commercially available as Montanide ISA-51 from Seppic S.A., Paris, France), or liposomal formulations may also be useful. It may also be useful to give the peptide conjugated to keyhole limpet hemocyanin, preferably also with an adjuvant.

The vaccine may be administered more than once. The therapeutically effective amount may be in the range of 0.20 mg to 5.0 mg, or in the range of 0.025 mg to 1.0 mg, or in the range of 2.0 mg to 5.0 mg of the peptide or the combination. Preferably, said peptide or combination is administered repeatedly, such as, for example, monthly, weekly, or every second week.

Vaccination results in cytotoxic T lymphocytes (CTL) responses stimulated by professional antigen presenting cells; once CTL are primed, there may be an advantage in enhancing MHC expression in tumor cells. It may also be useful to target the vaccine to specific cell populations, for example antigen presenting cells, either by the site of injection, use of targeting vectors and delivery systems, or selective purification of such a cell population from the patient and ex vivo administration of the peptide (for example dendritic cells may be sorted as described in Zhou et al (1995) Blood 86, 3295-3301; Roth et al (1996) Scand. J. Immunology 43, 646-651).

In another important aspect of the present invention, the peptide or combination (e.g. the vaccines) as used in the present invention are administered to a host either alone or in combination with another cancer therapy, preferably in order to inhibit or suppress the formation of tumors.

The peptides and combinations as used in the present invention may be used in the context of cancers, which may include lung cancer, head and neck cancer, breast cancer, pancreatic cancer, prostate cancer, renal cancer, esophageal cancer, bone cancer, testicular cancer, cervical cancer, gastrointestinal cancer, glioblastoma, leukemia, lymphomas, mantle cell lymphoma, pre-neoplastic lesions in the lung, colon cancer, melanoma, bladder cancer and any other neoplastic diseases. Preferred are renal cancer, colon cancer or glioblastoma.

In order to increase the effectiveness of a treatment with the peptides and combinations as used in the present invention, it may be desirable to combine these compositions with other agents effective in the treatment of those diseases and conditions. For example, the treatment of a cancer may be implemented using the peptides and combinations as used in the present invention and other anti-cancer therapies, such as anti-cancer agents.

The inventive use thus may further comprise treating the patient with a second anticancer agent, wherein the second anticancer agent is a therapeutic polypeptide, a nucleic acid encoding a therapeutic polypeptide, a chemotherapeutic agent, an immunotherapeutic agent, or a radiotherapeutic agent. The second anticancer agent may be administered simultaneously with the vaccine, or administered at a different time than the vaccine, preferably as one dosage before the vaccine.

Particularly preferred is the use of the peptide or combination according to the invention, which further comprises a treatment with at least one chemotherapeutic agent, such as, for example, an agent inactivating and/or eliminating CD4+CD25+ T cells in said patient, preferably CD4+CD25hi FOXP3+CD127lo T cells, such as, for example, cyclophosphamide.

Further preferred is the use of the peptide or combination according to the invention, wherein said treatment with said least one chemotherapeutic agent takes place before the administration of said peptide or combination, and is preferably given as a single dosage.

Particularly preferred is the use of the peptide or combination according to the invention, wherein said treatment with said least one chemotherapeutic agent takes place before the administration of said peptide or combination, and is preferably given as a single dosage, such as, for example, cyclophosphamide in a dosage of 300 mg/m2, preferably as a single infusion.

Also preferred is the use of the peptide or combination according to the invention, wherein said treatment is an adjuvant treatment following a prior TKI therapy, such as, for example, with sunitinib or sorafenib, and/or a prior cytokine therapy, such as, for example, with interferon or interleukin.

Most preferred is the use of the peptide or combination according to the invention, wherein said treatment comprises a cytokine therapy, followed by a single-dose cyclophosphamide therapy, followed by the administration of the vaccine as a 1st week priming with vaccinations at days 1,2,3,7, and then every two weeks for at least 6 months.

An "anti-cancer" agent is capable of negatively affecting cancer in a subject, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer. Preferred anti-cancer agents include chemotherapy agents. In the context of the present invention, it is contemplated that tumor-associated HLA-restricted peptide therapy based on the peptide or combination as used could be used similarly in conjunction with chemotherapeutic intervention.

The immunotherapeutic agent may be GM-CSF, CD40 ligand, anti-CD28 mAbs, anti-CTL-4 mAbs, anti-4-1BB (CD137) mAbs, and an oligonucleotide. The chemotherapeutic agent may be doxorubicin, daunorubicin, dactinomycin, mitoxantrone, cisplatin, procarbazine, mitomy-cin, carboplatin, bleomycin, etoposide, teniposide, mechlroethamine, cyclophosphamide, ifos-famide, melphalan, chlorambucil, ifosfamide, melphalan, hexamethylmelamine, thiopeta, busulfan, carmustine, lomustine, semustine, streptozocin, dacarbazine, adriamycin, 5-fluorouracil (5FU), camptothecin, actinomycin-D, hydrogen peroxide, nitrosurea, plicomycin, tamoxifen, taxol, transplatinum, vincristin, vinblastin, a TRAIL R1 and R2 receptor antibody or agonist, dolastatin-10, bryostatin, annamycin, Mylotarg®, sodium phenylacetate, sodium butyrate, methotrexate, dacitabine, imatinab mesylate (Gleevec®), interferon-alpah, bevacizumab, cetuximab, thalidomide, bortezomib, gefitinib, erlotinib, azacytidine, 5-AZA-2' deoxycytidine, Revlimid, 2C4, an anti-angiogenic factor, a signal transducer-targeting agent, interferon-y, IL-2 and IL-12.

Various combinations may be employed; for example, the peptide or combination or respective vaccine is "A" and the secondary therapy is "B": A/B/A, B/A/B, B/B/A, A/A/B, A/B/B, B/A/A, A/B/B/B, B/A/B/B, B/B/B/A, B/B/A/B, A/A/B/B, A/B/A/B, A/B/B/A, B/B/A/A, B/A/B/A, B/A/A/B, A/A/B, B/A/A/A, A/B/A/A, A/A/B/A. Administration of the peptide or combination as used in the present invention to a patient will follow general protocols for the administration of that particular secondary therapy, taking into account the toxicity, if any, of the tumor-associated HLA-restricted peptide treatment. It is expected that the treatment cycles would be repeated as necessary. It also is contemplated that various standard therapies, as well as surgical intervention, may be applied in combination with the described cancer cell. Nevertheless, preferred is a single dosage treatment as described further below.

Preferably, human monoclonal antibodies are further employed as a passive immunotherapy, as they produce few or no side effects in the patient.

Peptides (at least those containing peptide linkages between amino acid residues) may be synthesized by the Fmoc-polyamide mode of solid-phase peptide synthesis as disclosed by Lu et al (1981) J. Org. Chem. 46, 3433 and references therein. Temporary N-amino group protection is afforded by the 9-fluorenylmethyloxycarbonyl (Fmoc) group. Repetitive cleavage of this highly base-labile protecting group is effected using 20% piperidine in N,N-dimethylformamide. Side-chain functionalities may be protected as their butyl ethers (in the case of serine threonine and tyrosine), butyl esters (in the case of glutamic acid and aspartic acid), butyloxycarbonyl derivative (in the case of lysine and histidine), trityl derivative (in the case of cysteine) and 4-methoxy-2,3,6-trimethylbenzenesulphonyl derivative (in the case of arginine). Where glutamine or asparagine are C-terminal residues, use is made of the 4,4'-dimethoxybenzhydryl group for protection of the side chain amido functionalities. The solid-phase support is based on a polydimethyl-acrylamide polymer constituted from the three monomers dimethylacrylamide (backbone-monomer), bisacryloylethylene diamine (cross linker) and acryloylsarcosine methyl ester (functionalizing agent). The peptide-to-resin cleavable linked agent used is the acid-labile 4-hydroxymethyl-phenoxyacetic acid derivative. All amino acid derivatives are added as their preformed symmetrical anhydride derivatives with the exception of asparagine and glutamine, which are added using a reversed N,N-dicyclohexyl-carbodiimide/hydroxybenzotriazole mediated coupling procedure. All coupling and deprotection reactions are monitored using ninhydrin, trinitrobenzene sulphonic acid or isotin test procedures. Upon completion of synthesis, peptides are cleaved from the resin support with concomitant removal of side-chain protecting groups by treatment with 95% trifluoroacetic acid containing a 50% scavenger mix. Scavengers commonly used are ethandi-thiol, phenol, anisole and water, the exact choice depending on the constituent amino acids of the peptide being synthesized. Also a combination of solid phase and solution phase methodologies for the synthesis of peptides is possible (see, for example, Bruckdorfer T, Marder O, Albericio F. From production of peptides in milligram amounts for research to multi-tons quantities for drugs of the future. Curr Pharm Biotechnol. 2004 February; 5(1):29-43 and the references as cited therein).

Trifluoroacetic acid is removed by evaporation in vacuo, with subsequent trituration with diethyl ether affording the crude peptide. Any scavengers present are removed by a simple extraction procedure which on lyophilization of the aqueous phase affords the crude peptide free of scavengers. Reagents for peptide synthesis are generally available from Calbiochem-Novabiochem (UK) Ltd, Nottingham NG7 2QJ, UK.

Purification may be effected by any one, or a combination of, techniques such as size exclusion chromatography, ion-exchange chromatography, hydrophobic interaction chromatography and (usually) reverse-phase high performance liquid chromatography using acetonitrile/water gradient separation.

Analysis of peptides may be carried out using thin layer chromatography, reverse-phase high performance liquid chromatography, amino-acid analysis after acid hydrolysis and by fast atom bombardment (FAB) mass spectrometric analysis, as well as MALDI and ESI-mass spectrometric analysis.

It will be appreciated that certain host cells are useful in the preparation of the peptides as used in the invention, for example bacterial, yeast and insect cells. However, other host cells may be useful in certain therapeutic methods. For example, antigen-presenting cells, such as dendritic cells, may usefully be used to express the peptides as used in the invention such that they may be loaded into appropriate MHC molecules.

A further aspect of the invention then provides the use of the peptide or combination according to the present invention for producing activated cytotoxic T lymphocytes (CTL) in vitro, comprising contacting CTL with peptide or combination loaded human class I or II MHC molecules expressed on the surface of a suitable antigen-presenting cell for a period of time sufficient to activate said CTL in an antigen specific manner.

A further aspect of the invention then provides a method of killing target cells in a patient which target cells aberrantly express a polypeptide comprising an amino acid sequence of the invention, the method comprising administering to the patient an effective amount of a peptide according to the invention, or an effective amount of a polynucleotide or an expression vector encoding a said peptide, wherein the amount of said peptide or amount of said polynucleotide or expression vector is effective to provoke an anti-target cell immune response in said patient. The target cell is typically a tumor or cancer cell.

It will be appreciated that, with respect to the methods of killing target cells in a patient, it is particularly preferred that the target cells are cancer cells as described above, more preferably renal or colon cancer cells.

A further aspect of the invention includes in particular the use of the peptides of the invention for active in vivo vaccination; for manipulation of autologous dendritic cells in vitro followed by introduction of the so-manipulated dendritic cells in vivo to activate CTL responses; to activate autologous CTL in vitro followed by adoptive therapy (i.e. the so-manipulated CTL are introduced into the patient); and to activate CTL from healthy donors (MHC matched or mismatched) in vitro followed by adoptive therapy.

A further aspect of the invention then relates to the use of the peptide or combination according to the invention as a diagnostic tool in order to detect and/or monitor an activation or modulation of the immune system of a patient. In this aspect, the peptides can be used to detect a response to an anti-cancer treatment, in particular a non-peptide based treatment, or any other suitable treatment resulting in immune system activation or modulation. For the diagnosis, the peptides can be labeled. Furthermore, antibodies against the peptides (or combinations) can also be used. The diagnosis can be performed in vivo or in vitro.

A further aspect of the invention then relates to the use of the peptide or combination according to the invention as a diagnostic tool in the diagnosis of cancer. Basically, the presence of the peptides or a combination thereof in the patient indicates cancer. For example, pre-vaccination responses against CCN-001 and CEA-004 were found in certain cancer patients. Again, for the diagnosis, the peptides can be labeled. Furthermore, antibodies against the peptides (or combinations) can also be used. The diagnosis can be performed in vivo or in vitro.

The phrase "isolated" refers to material which is substantially or essentially free from components which normally accompany the material as it is found in its native state. Thus, isolated peptides in accordance with the invention preferably do not contain materials normally associated with the peptides in their in situ environment.

A further aspect of the invention then relates to a peptide comprising a sequence selected from the group of SEQ ID NO: 5 or SEQ ID NO: 6, or a variant thereof that is at least 85% homologous to SEQ ID NO: 5 or SEQ ID NO: 6, or a variant thereof that induces T cells cross-reacting with said variant peptide; wherein said peptide is not the respective (underlying) full-length polypeptide. Preferably, said peptide is selected from a peptide having a specific HLA-subtype, such as HLA-A*02.

A further aspect of the invention then relates to a nucleic acid, encoding a peptide according to SEQ ID NO: 5 or SEQ ID NO: 6 or a variant thereof according to the present invention or an expression vector capable of expressing said nucleic acid. In another aspect thereof, the present invention relates to a host cell comprising the nucleic acid or the expression vector according to the present invention, wherein said host cell preferably is an antigen presenting cell, in particular a dendritic cell or antigen presenting cell.

In another aspect thereof, the present invention relates to an in vitro method for producing activated cytotoxic T lymphocytes (CTL), comprising contacting in vitro CTL with antigen loaded human class I MHC molecules expressed on the surface of a suitable antigen-presenting cell or an artificial construct mimicking an antigen-presenting cell for a period of time sufficient to activate said CTL in an antigen specific manner, wherein said antigen is a peptide according to SEQ ID NO: 5 or SEQ ID NO: 6 of the present invention.

In yet another aspect thereof, the present invention relates to a kit, comprising: (a) a container that contains a pharmaceutical composition containing a peptide according to SEQ ID NO: 5 or SEQ ID NO: 6 according to the present invention, the nucleic acid or the expression vector according to the present invention, a cell according to the present invention, or an activated cytotoxic T lymphocyte according to the present invention, in solution or in lyophilized form; (b) optionally, a second container containing a diluent or reconstituting solution for the lyophilized formulation; (c) optionally, at least one peptide selected from the group consisting of the peptides according to SEQ ID NO: 1 to SEQ ID NO: 4 and SEQ ID NO: 7 to SEQ ID NO: 26, and (d) optionally, instructions for the use of the solution and/or the reconstitution and/or use of the lyophilized formulation.

In yet another aspect thereof, the present invention relates to an antibody that specifically binds to a human major histocompatibility complex (MHC) class I being complexed with a HLA-restricted antigen according to SEQ ID NO: 5 or SEQ ID NO: 6 according to the present invention, wherein the antibody preferably is a polyclonal antibody, monoclonal antibody and/or a chimeric antibody.

A further aspect of the invention then relates to a method for treating a cancerous disease, based on the use of the peptide or combination or vaccines as described above.

Other objects, features and advantages of the present invention will become apparent from the following examples. It should be understood, however, that the specific examples, while indicating preferred embodiments of the invention, are given by way of illustration only, since various changes and modifications within the spirit and scope of the invention will become apparent to those skilled in the art from this detailed description. For the purposes of the present invention, all references as cited herein are incorporated by reference in their entireties.

SEQ ID NO: 1 to 26 show peptides as used in the context of the present invention.

SEQ ID NO: 5 and SEQ ID NO: 6 show cyclin peptides according to the present invention.

SEQ ID NO: 27 shows the amino acid sequence of cyclin D1.

EXAMPLES

1. Identification and Characterization of Peptides as Used According to the Present Invention In general, the peptides as used according to the present invention were identified using the XPRESIDENT® technology as described (see, for example, Weinschenk et al. Integrated Functional Genomics Approach for the Design of Patient-individual Antitumor Vaccines, CANCER RESEARCH 62, 5818-5827, Oct. 15, 2002) on the basis of renal cancer cells. The average overexpression of cyclin D1

(CCND1) in ccRCC against the average expression in normal tissues was 3.0-fold, and 5.7-fold in primary tumors and 5.4-fold in metastases. 55% of primary tumors showed an overexpression against normal kidney.

2. HLA-Restriction of the Peptides as Identified

For CCN-001 and CCN-002, a good binding to HLA A*02 was predicted using the SYFPEITHI routine (Rammensee et al., 1997; Rammensee et al., 1999). Good binding of CCN-001 to HLA A*0201 was confirmed by an ELISA-based method (Sylvester-Hvid et al., 2002). For CCN-004, a high binding to HLA-A*26 and practically no binding to HLA-A*02 was found.

For the peptide CCN-006, only a weak binding to HLA-A*02 was predicted. Indeed, CCN-006 seems to be a HLA-A*68 binder. The new peptide CCN-007 is a moderate binder to HLA A*02. CCN-003 binds to HLA class-II, and thus appears DRB1*0401 restricted.

For the following clinical study, the peptide CCN-001 was chosen. Nevertheless, the skilled person will be aware that also all other peptides or a combination thereof as described herein can be used, and that the examples can be readily adjusted as needed in accordance with these peptides or a combination thereof as described herein.

3. Clinical Study Using the Peptides and Combination of the Invention

Some patients received a prior TKI therapy with sunitinib or sorafenib, others a prior cytokine therapy with interferon or interleukin. Then, two groups of patients were formed, one receiving cyclophosphamide (300 mg/m2) as a single infusion before the vaccination with the vaccine containing one of the cyclin D1 peptides (in this case, vaccine IMA901 of immatics Biotechnologies, containing CCN-001, 17 vaccinations over a course of 9 months), and the other not receiving cyclophosphamide before the vaccination with the vaccine containing one of the cyclin D1 peptides (again IMA901, 17 vaccinations over a course of 9 months).

Both patient groups were followed up for progression-free survival (PFS) and overall survival (OS).

4. Results of the Study

It was found that the vaccine overall is safe and very well tolerated by the patients. The only common adverse effect was a local injection-site reaction.

The Disease Control Rate (DCR) at 6 months met the expectations (i.e. the protocol defined a clinically relevant effect in post-cytokine patients as DCR at 6 months >30%).

The vaccine containing the cyclin peptide showed a better OS than other 2nd line post cytokine treatments (Sutent® or Nexavar®).

A better PFS and OS was found in patients with prior cytokine therapy compared to patients with prior TKI therapy. Progression-free survival (PFS) analysis indicates delayed positive effect when compared to placebo arms of another trial. Overall survival (OS) appeared to be longer compared with data for TKI (i.e. sorafinib and sunitinib in second line mRCC).

There was a significant correlation of multi-peptide immune responses with OS in the overall population.

More surprisingly, a prior low-dose cyclophosphamide treatment further significantly improved the outcome of the treatment using the vaccine. As expected, the low-dose cyclophosphamide reduced the number of regulatory T cells.

Comparison between survival of patients responding against CCN-001 versus non-CCN-001-responding patients showed significant longer survival for patients in which a CCN-001 response could be induced by vaccination. This favorable effect of T cell response against CCN-001 was even more evident within the patient group pretreated with cyclophosphamide.

The invention claimed is:

1. A method of treating a cyclin D1 expressing cancer, comprising steps of:
    (a) treating a subject in need thereof with a single dosage infusion of at least one chemotherapeutic agent comprising 300 mg/m² of cyclophosphamide, wherein the chemotherapeutic agent inactivates and/or eliminates CD4⁺ CD25⁺ regulatory T cells in said subject; and subsequent to such treating step,
    (b) administering to the subject a pharmaceutical composition comprising a peptide consisting essentially of an amino acid sequence selected from the group consisting of SEQ ID NO: 1 and SEQ ID NO: 2 and a peptide consisting essentially of an amino acid sequence of SEQ ID NO: 18; wherein said peptides have fewer than 50 residues.

2. The method of claim 1, wherein said pharmaceutical composition is administered repeatedly.

3. The method of claim 2, wherein said pharmaceutical composition is administered monthly, weekly, or twice a week.

4. The method of claim 1, wherein the pharmaceutical composition is administered as an adjuvant treatment, following a prior tyrosine kinase inhibitor therapy and/or a prior cytokine therapy, wherein said tyrosine kinase inhibitor therapy and/or cytokine therapy occurs prior to step (a).

5. The method of claim 4, wherein the tyrosine kinase inhibitor therapy comprises sunitinib and/or sorafenib and the cytokine therapy comprises an interferon and/or an interleukin.

6. The method of claim 1, comprising: a cytokine therapy that is administered to the patient before step (a), and wherein the pharmaceutical composition in step (b) is administered as a first week priming vaccination at days 1, 2, 3, and 7 and then administered every two weeks for at least 6 months.

7. The method according to claim 1, wherein said pharmaceutical composition further comprises a peptide consisting essentially of an amino acid sequence of SEQ ID NO: 6.

8. The method according to claim 1, wherein said pharmaceutical composition further comprises at least one peptide consisting essentially of an amino acid sequence selected from the group consisting of SEQ ID NO:6 to SEQ ID NO: 17.

9. The method according to claim 1, wherein said cyclin D1 expressing cancer is selected from the group consisting of lung cancer, head and neck cancer, breast cancer, pancreatic cancer, prostate cancer, renal cancer, esophageal cancer, bone cancer, testicular cancer, cervical cancer, gastrointestinal cancer, glioblastoma, leukemia, lymphoma, mantle cell lymphoma, pre-neoplastic lesions in the lung, colon cancer, melanoma, and bladder cancer.

10. The method according to claim 1, wherein said pharmaceutical composition is administered in the form of an anti-cyclin D1 expressing cancer vaccine.

11. The method according to claim 1, wherein said pharmaceutical composition comprises at least one adjuvant.

12. The method according to claim 1, wherein the pharmaceutical composition comprises the adjuvant GM-CSF.

13. The method according to claim 1, wherein the pharmaceutical composition further comprises at least one tumor associated peptide which is not derived from cyclin D1.

14. The method according to claim 1, wherein the pharmaceutical composition further comprises at least one tumor associated peptide selected from the group consisting of SEQ ID NO: 19 to SEQ ID NO: 26.

15. The method according to claim 13, wherein the at least one tumor associated peptide which is not derived from cyclin D1 is chosen based on its ability to bind to a different HLA-molecule, as compared with the at least one peptide selected from the group consisting of SEQ ID NO: 1, SEQ ID NO: 2, and SEQ ID NO: 6 to SEQ ID NO: 18.

* * * * *